US012780816B2

(12) United States Patent
Xu et al.

(10) Patent No.: US 12,780,816 B2
(45) Date of Patent: Nov. 3, 2026

(54) SOLID FORMS OF A BENZTHIAZOLE-PIPERAZINYL-OXAZOLE COMPOUND AND METHODS OF USE THEREOF

(71) Applicant: Hepagene Therapeutics (HK) Limited, Hong Kong (CN)

(72) Inventors: Xiaodong Xu, Hong Kong (CN); Cheng Mo, Hong Kong (CN); Shijia Chen, Hong Kong (CN)

(73) Assignee: Hepagene Therapeutics (HK) Limited, Hong Kong (CN)

( * ) Notice: Subject to any disclaimer, the term of this patent is extended or adjusted under 35 U.S.C. 154(b) by 273 days.

(21) Appl. No.: 18/728,753

(22) PCT Filed: Jan. 12, 2023

(86) PCT No.: PCT/US2023/010716
§ 371 (c)(1),
(2) Date: Jul. 12, 2024

(87) PCT Pub. No.: WO2023/137135
PCT Pub. Date: Jul. 20, 2023

(65) Prior Publication Data

US 2025/0066346 A1 Feb. 27, 2025

(30) Foreign Application Priority Data

Jan. 17, 2022 (WO) ................ PCT/CN2022/072314

(51) Int. Cl.

| | |
|---|---|
| ***C07D 417/12*** | (2006.01) |
| ***A61K 31/496*** | (2006.01) |
| ***A61P 31/12*** | (2006.01) |
| ***C07C 309/04*** | (2006.01) |
| ***C07C 309/05*** | (2006.01) |
| ***C07D 417/14*** | (2006.01) |

(52) U.S. Cl.
CPC .......... *C07D 417/12* (2013.01); *A61K 31/496* (2013.01); *C07C 309/04* (2013.01); *C07C 309/05* (2013.01)

(58) Field of Classification Search
CPC .. C07D 417/12; C07D 417/14; C07C 309/04; C07C 309/05; A61K 31/496; A61P 31/12
See application file for complete search history.

(56) References Cited

U.S. PATENT DOCUMENTS

2019/0276465 A1* 9/2019 Xu ............................ A61P 3/06

FOREIGN PATENT DOCUMENTS

WO WO-2009/127321 A1 10/2009
WO WO-2018/067704 A1 4/2018

OTHER PUBLICATIONS

International Search Report and Written Opinion on PCT/US2023/010716 Dtd Mar. 28, 2023, 9 pages.

* cited by examiner

*Primary Examiner* — Kamal A Saeed
*Assistant Examiner* — Sagar Patel
(74) *Attorney, Agent, or Firm* — Foley & Lardner LLP

(57) ABSTRACT

The present technology provides crystalline free base and crystalline hydrochloride, hydrobromide, edisylate, and mesylate salts of (R)-2-(4-((5-cyclopropyl-3-(2,6-dichlorophenyl)isoxazol-4-yl)methyl)-2-methylpiperazin-1-yl)-4-methoxybenzo[d]thiazole-6-carboxylic acid. The present technology further provides methods for preparing the various forms, compositions containing them, and methods related to modulation of FXR. In particular, the present crystalline compounds and compositions may be used to treat FXR-mediated disorders and conditions, including, e.g., hepatitis B, liver disease, hyperlipidemia, hypercholesteremia, obesity, metabolic syndrome, cardiovascular disease, gastrointestinal disease, and atherosclerosis, and renal disease.

36 Claims, 18 Drawing Sheets

SOLID FORMS OF A BENZTHIAZOLE-PIPERAZINYL-OXAZOLE COMPOUND AND METHODS OF USE THEREOF

CROSS-REFERENCE TO RELATED APPLICATIONS

This application is a U.S. National Phase Application under 35 U.S.C. § 371 of International Application No. PCT/US2023/010716, filed on Jan. 12, 2023, which claims the benefit of and priority to International Patent Application No. PCT/CN2022/072314, filed on Jan. 17, 2022, the contents of each of which are incorporated herein by reference in their entirety.

FIELD OF INVENTION

The present technology relates to generally to crystalline forms of (R)-2-(4-((5-cyclopropyl-3-(2,6-dichlorophenyl)isoxazol-4-yl)methyl)-2-methylpiperazin-1-yl)-4-methoxybenzo[d]thiazole-6-carboxylic acid, its salts, methods for preparing them, compositions containing them, and methods of treatment employing them.

BACKGROUND (R)-2-(4-((5-cyclopropyl-3-(2,6-dichlorophenyl)isoxazol-4-yl)methyl)-2-methylpiperazin-1-yl)-4-methoxybenzo[d]thiazole-6-carboxylic acid (described in PCT/US2017/058802, filed Oct. 27, 2017, and incorporated by reference in its entirety herein) has the structure of Compound I:

I

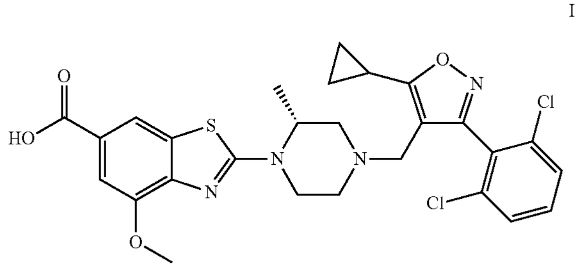 [SMILES: COc1cc(C(=O)O)cc2sc(N3CCN(Cc4c(-c5c(Cl)cccc5Cl)noc4C4CC4)C[C@H]3C)nc12]

Compound I is a modulator of farnesoid X receptor (FXR) and is useful in the treatment of FXR-mediated disorders and conditions, including, e.g., hepatitis B, liver disease, hyperlipidemia, hypercholesteremia, obesity, metabolic syndrome, cardiovascular disease, gastrointestinal disease, atherosclerosis, and renal disease.

It is well known that the crystalline form of the active pharmaceutical ingredient (API) of a particular drug is often an important determinant of the drug's ease of preparation, hygroscopicity, stability, solubility, storage stability, ease of formulation, rate of dissolution in gastrointestinal fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc. are deemed to be critical. In other situations, a different form may be preferred for greater dissolution rate and/or superior bioavailability. It is not yet possible to predict whether a particular compound or salt of a compound will form polymorphs (i.e., crystal structures), whether any such polymorphs will be suitable for commercial use in a therapeutic composition, or which polymorphs will display such desirable properties.

SUMMARY

Provided herein are crystal forms of Compound I, compositions including the crystal forms, and methods of preparing the crystal forms and compositions. The present technology further provides methods of using the crystal forms of Compound I and compositions thereof to treat FXR-mediated disorders or conditions, including, but not limited to hepatitis B, liver disease, hyperlipidemia, hypercholesteremia, obesity, metabolic syndrome, cardiovascular disease, gastrointestinal disease, atherosclerosis, or renal disease. For example, the disorder or condition may be a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

DETAILED DESCRIPTION

In one aspect, the present technology provides a crystalline compound selected from a crystalline free base or a crystalline hydrochloride, hydrobromide, edisylate (1,2-ethanedisulfonate), or mesylate (methanesulfonate) salt of the compounds of Formula I:

I

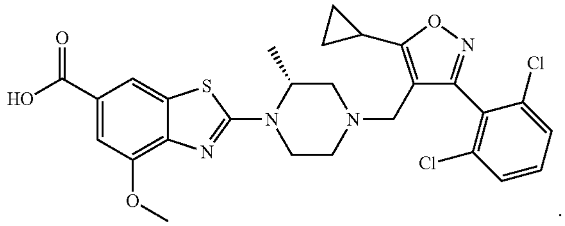

.

Figure 3:
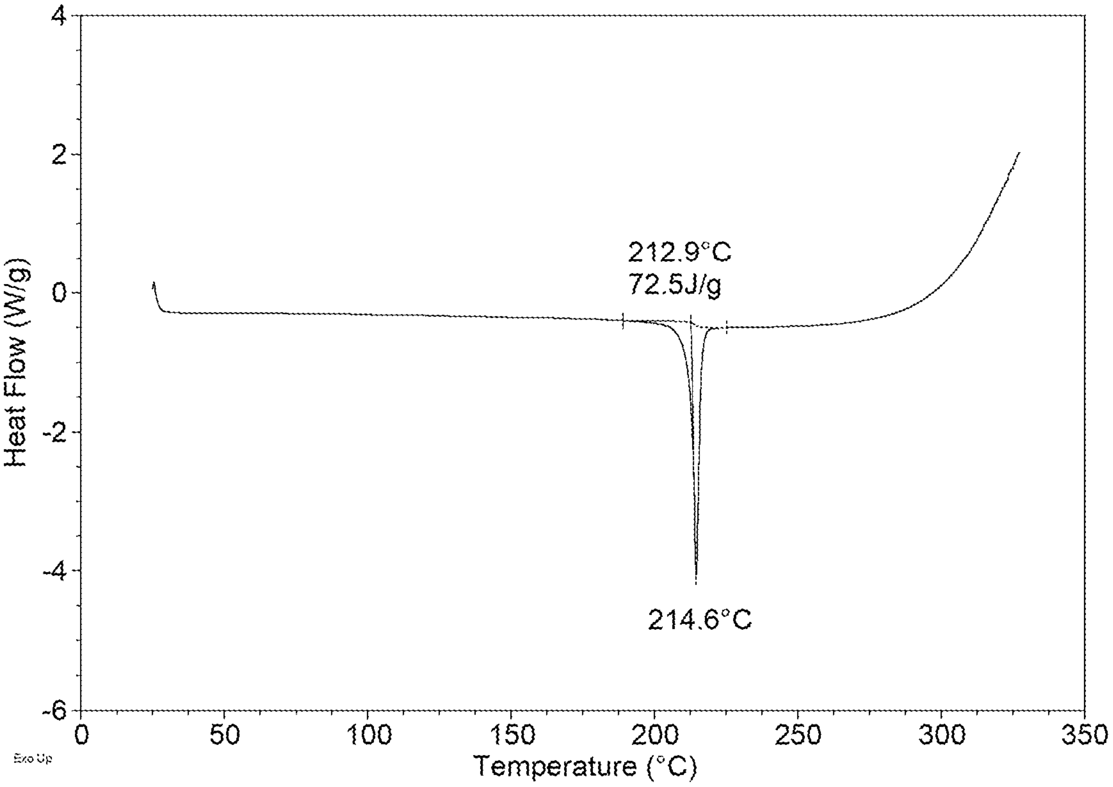
FIG. 3 provides a differential scanning calorimetry (DSC) thermogram of the crystalline free base of Compound I (form A), according to the examples.

In one embodiment, the present technology provides the crystalline free base (herein referred to as "form A" of Compound I). In any embodiment, the crystalline free base may have an XRPD including a characteristic peak, in terms of 2θ, at about 14.48°. In any embodiment, the crystalline free base may have an XRPD including one or more characteristic peaks, in terms of 2θ, at about 14.48°, about 13.48°, and about 24.77°. In any embodiment, the crystalline free base may further include have one or more characteristic peaks, in terms of 2θ, at about 23.42°, about 6.77°, and about 27.12°. In any embodiment, the crystalline free base may further include have one or more characteristic peaks, in terms of 2θ, at about 18.89°, about 21.24°, about 21.93°, and about 20.63°. In any embodiment, the crystalline free base may have an XRPD substantially as shown in FIG. 3.

Figure 6:
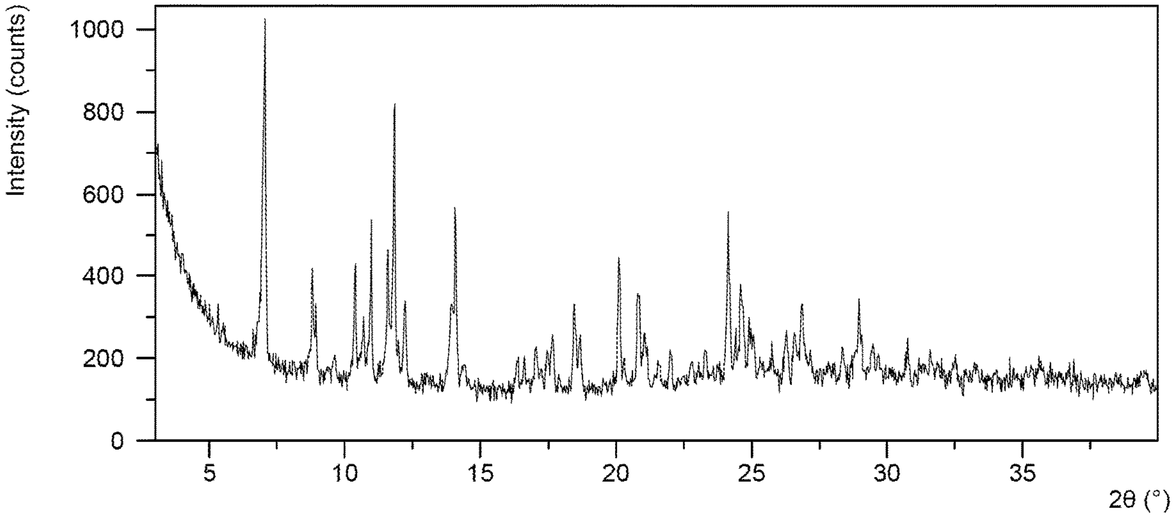
FIG. 6 provides an XRPD spectrum of the crystalline hydrochloride salt of Compound I (form B), according to the examples.

In one embodiment, the present technology provides the crystalline hydrochloride salt of Compound I (herein referred to as "form B" of Compound I). In any embodiment, the crystalline hydrochloride salt may have an XRPD including a characteristic peak, in terms of 2θ, at about 7.04°. In any embodiment, the crystalline hydrochloride salt may have an XRPD including one or more characteristic peaks, in terms of 2θ, at about 7.04°, about 11.83°, and about 14.08°. In any embodiment, the crystalline hydrochloride salt may further include have one or more characteristic peaks, in terms of 2θ, at about 10.97°, about 24.14°, and about 37.65°. In any embodiment, the crystalline hydrochloride salt may further include have one or more characteristic peaks, in terms of 2θ, at about 36.95°, about 10.98°, about 8.81°, and about 24.62°. In any embodiment, the crystalline hydrochloride salt may have an XRPD substantially as shown in FIG. 6.

Figure 22:
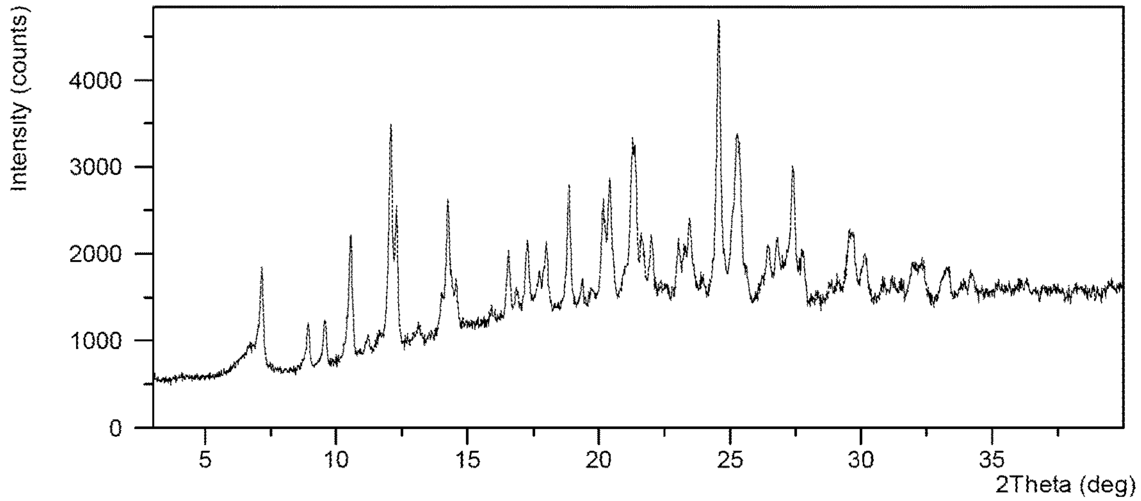
FIG. 22 provides an XRPD spectrum of the crystalline hydrochloride salt of Compound I (form C), according to the examples.

In one embodiment, the present technology provides the crystalline hydrochloride salt of Compound I (herein referred to as "form C" of Compound I). In any embodiment, form C may have an XRPD including a characteristic peak, in terms of 2θ, at about 24.57°. In any embodiment, form C may have an XRPD including one or more characteristic peaks, in terms of 2θ, at about 24.57°, about 25.25°, and about 12.08°. In any embodiment, form C may further include have one or more characteristic peaks, in terms of 2θ, at about 21.28°, about 21.40°, and about 20.44°. In any embodiment, form C may further include have one or more characteristic peaks, in terms of 2θ, at about 18.87°, about 14.25°, about 27.40°, and about 12.30°. In any embodiment, form C may have an XRPD substantially as shown in FIG. 22.

Figure 11:
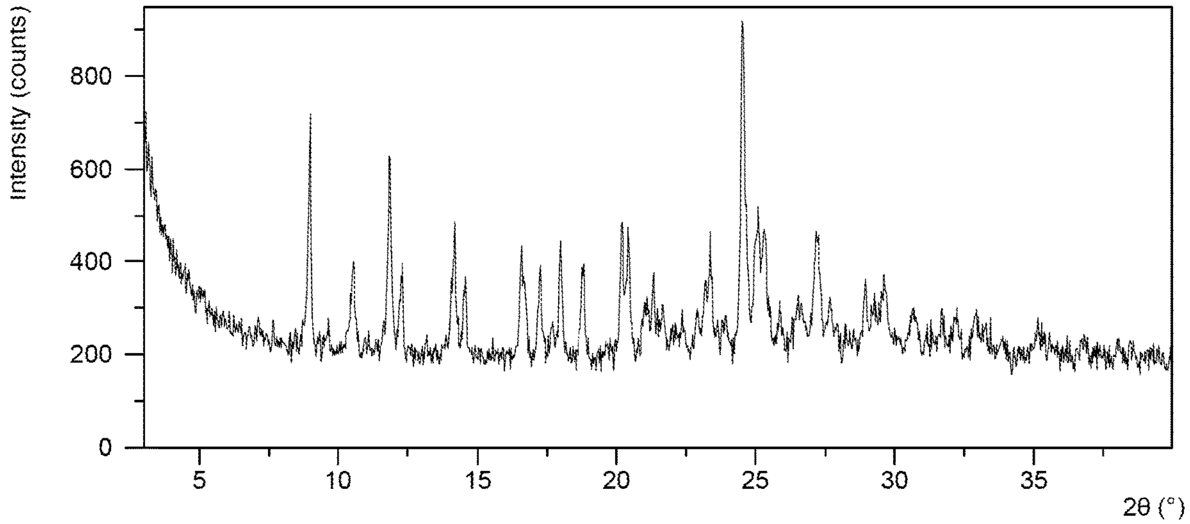
FIG. 11 provides an XRPD spectrum of the crystalline hydrobromide salt of Compound I (form D), according to the examples.

In one embodiment, the present technology provides the crystalline hydrobromide salt of Compound I (herein referred to as "form D" of Compound I). In any embodiment, the hydrobromide salt may have an XRPD including a characteristic peak, in terms of 2θ, at about 24.53°. In any embodiment, the crystalline hydrobromide salt may have an XRPD including one or more characteristic peaks, in terms of 2θ, at about 24.53°, about 8.99°, and about 11.85°. In any embodiment, the crystalline hydrobromide salt may further include have one or more characteristic peaks, in terms of 2θ, at about 20.20°, about 20.44°, and about 25.04°. In any embodiment, the crystalline hydrobromide salt may further include have one or more characteristic peaks, in terms of 2θ, at about 14.18°, about 17.97°, about 27.21°, and about 23.28°. In any embodiment, the crystalline hydrobromide salt may have an XRPD substantially as shown in FIG. 11.

Figure 23:
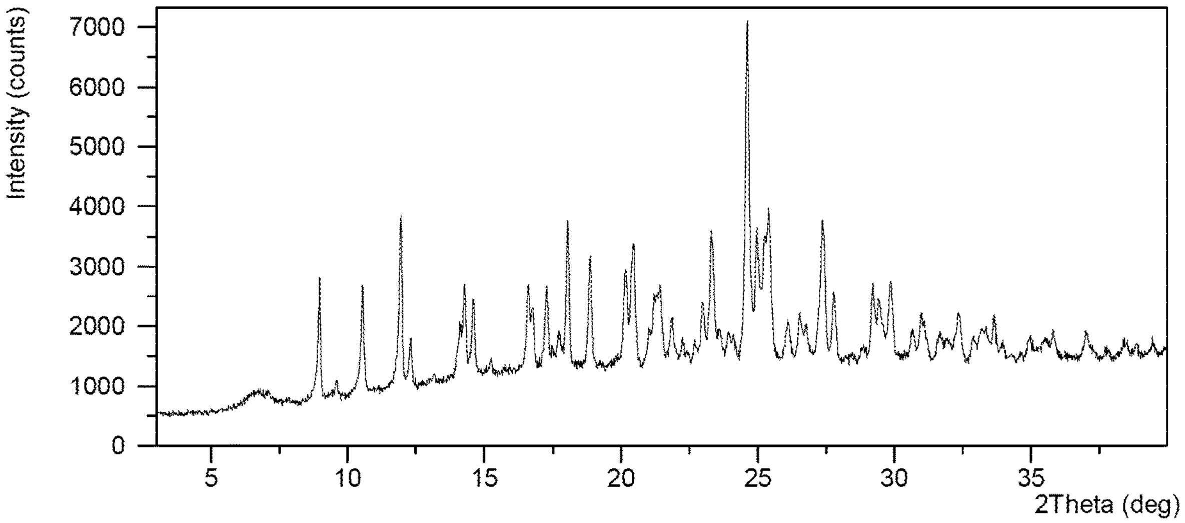
FIG. 23 provides an XRPD spectrum of the crystalline hydrobromide salt of Compound I (form E), according to the examples.

In one embodiment, the present technology provides the crystalline hydrobromide salt of Compound I (herein referred to as "form E" of Compound I). In any embodiment, form E may have an XRPD including a characteristic peak, in terms of 2θ, at about 24.60°. In any embodiment, form E may have an XRPD including one or more characteristic peaks, in terms of 2θ, at about 24.60°, about 25.41°, and about 11.95°. In any embodiment, form E may further include have one or more characteristic peaks, in terms of 2θ, at about 18.04°, about 27.38°, and about 24.96°. In any embodiment, form E may further include have one or more characteristic peaks, in terms of 2θ, at about 23.29°, about 25.24°, about 20.47°, and about 18.89°. In any embodiment, form E may have an XRPD substantially as shown in FIG. 23.

Figure 16:
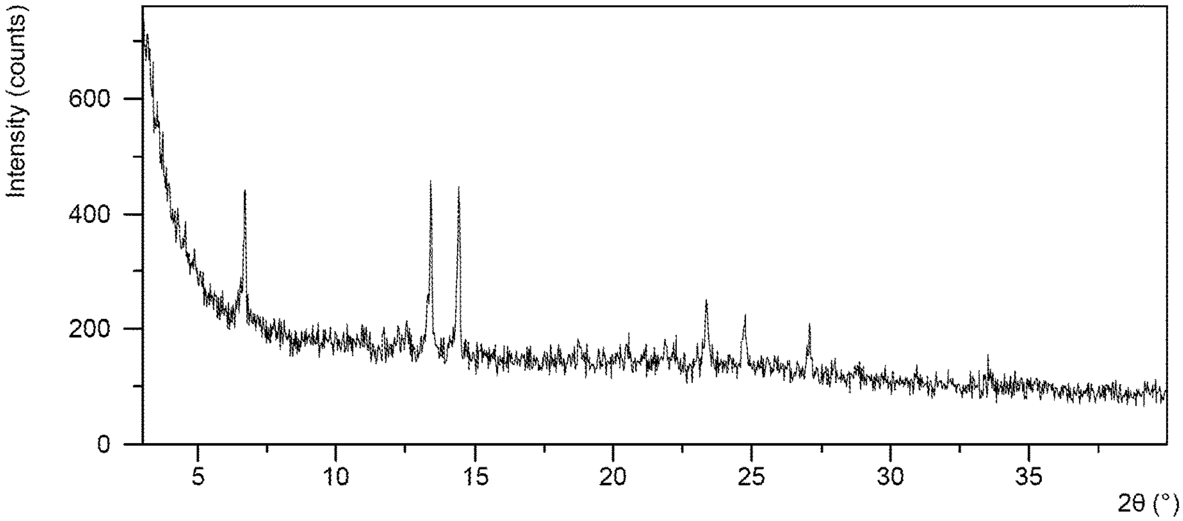
FIG. 16 provides an XRPD spectrum of the crystalline edisylate salt of Compound I (form F), according to the examples.

In one embodiment, the present technology provides the crystalline edisylate salt of Compound I (herein referred to as "form F" of Compound I). In any embodiment, the crystalline edisylate salt may have an XRPD including a characteristic peak, in terms of 2θ, at about 13.41°. In any embodiment, the crystalline edisylate salt may have an XRPD including one or more characteristic peaks, in terms of 2θ, at about 13.41°, about 14.42°, and about 6.69°. In any embodiment, the crystalline edisylate salt may further include have one or more characteristic peaks, in terms of 2θ, at about 23.36°, about 24.72°, and about 27.06°. In any embodiment, the crystalline edisylate salt may have an XRPD substantially as shown in FIG. 16.

Figure 19:
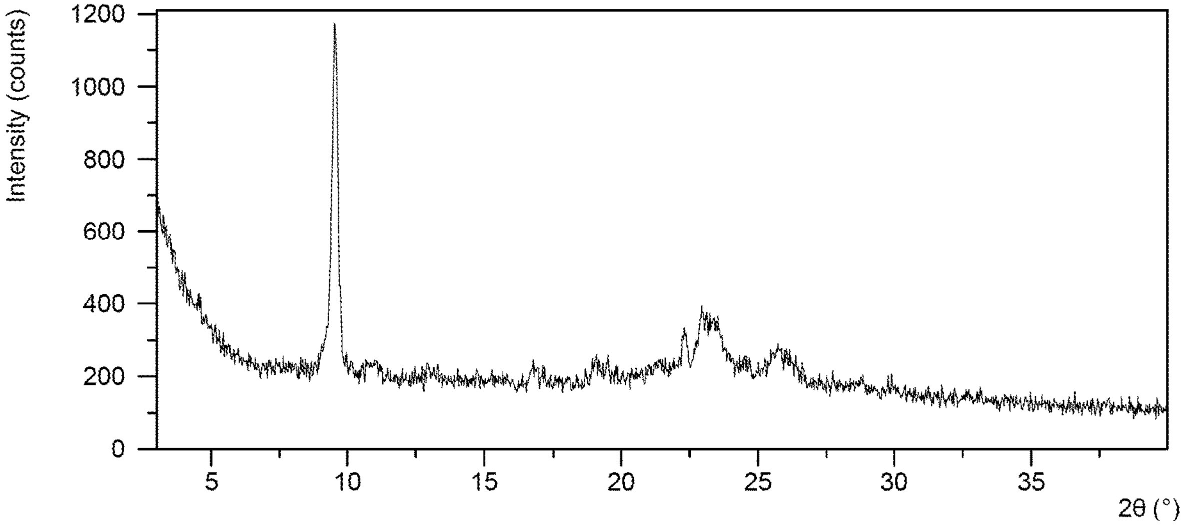
FIG. 19 provides an XRPD spectrum of the crystalline mesylate salt of Compound I (form G), according to the examples.

In one embodiment, the present technology provides the crystalline mesylate salt of Compound I (herein referred to as "form G" of Compound I). In any embodiment, the crystalline mesylate salt may have an XRPD including a characteristic peak, in terms of 2θ, at about 9.54°. In any embodiment, the crystalline mesylate salt may have an XRPD including one or more characteristic peaks, in terms of 2θ, at about 9.54°, about 22.96°, and about 22.33°. In any embodiment, the crystalline mesylate salt may further include have one or more characteristic peaks, in terms of 2θ, at about 25.80°, about 16.84°, and about 19.23°. In any embodiment, the crystalline mesylate salt may have an XRPD substantially as shown in FIG. 19.

Figure 8:
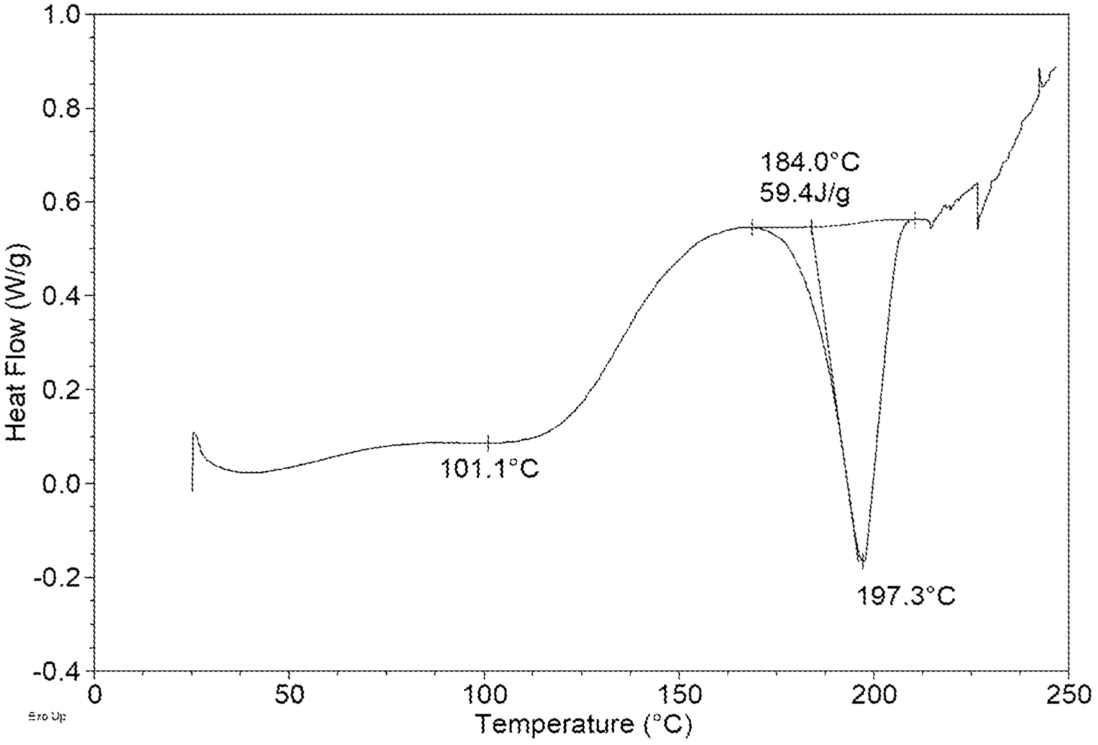
FIG. 8 provides a DSC thermogram of the crystalline hydrochloride salt of Compound I (form B), according to the examples.
Figure 13:
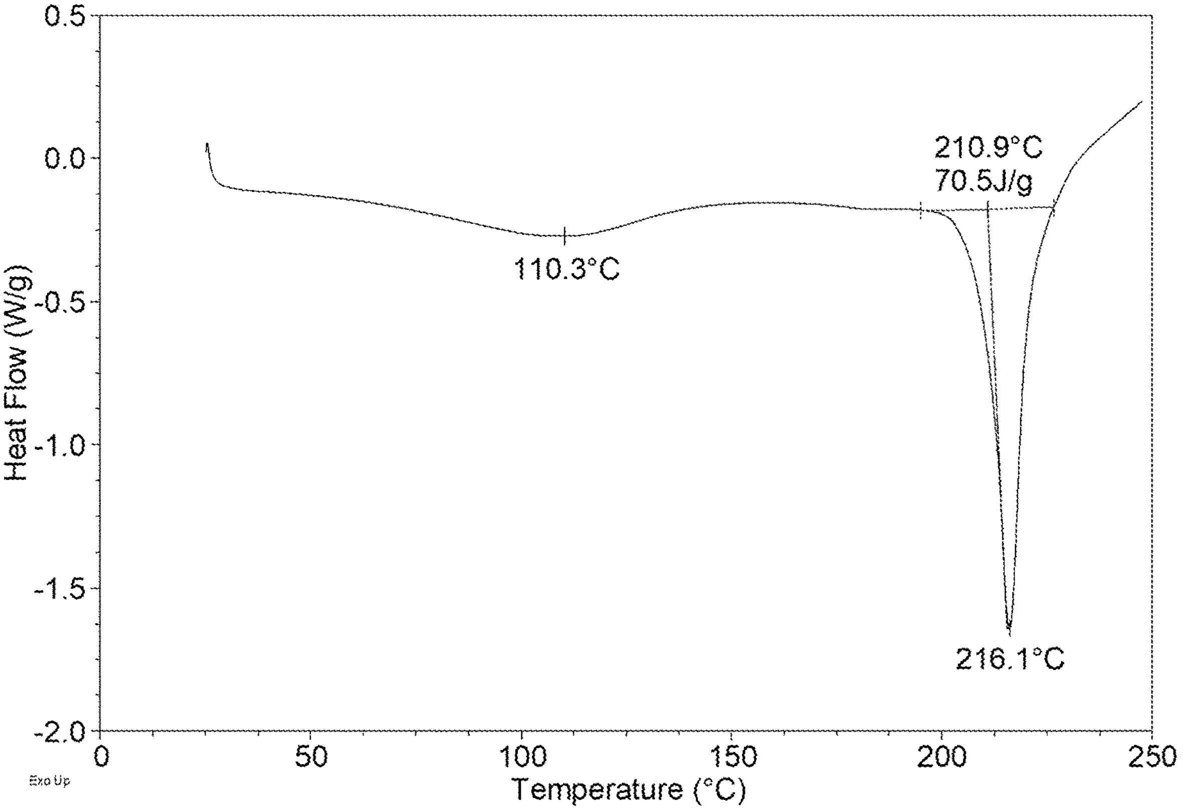
FIG. 13 provides a DSC thermogram of the crystalline hydrobromide salt of Compound I (form D), according to the examples.
Figure 18:
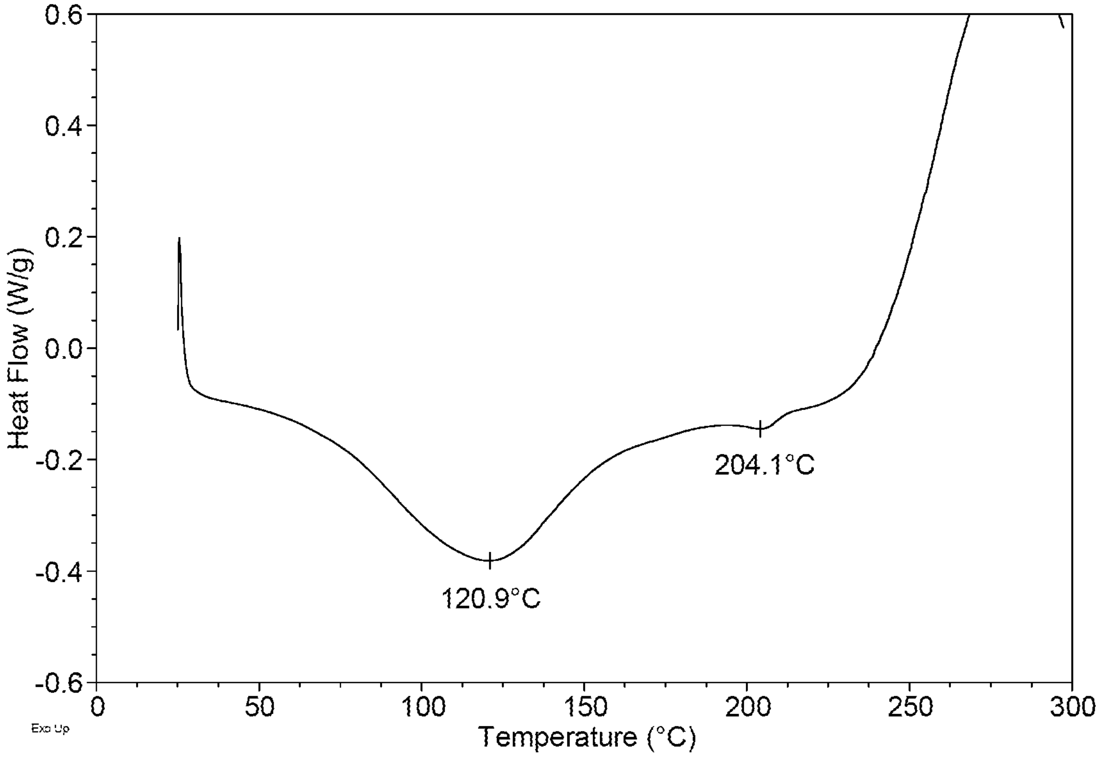
FIG. 18 provides a DSC thermogram of the crystalline edisylate salt of Compound I (form F), according to the examples.
Figure 21:
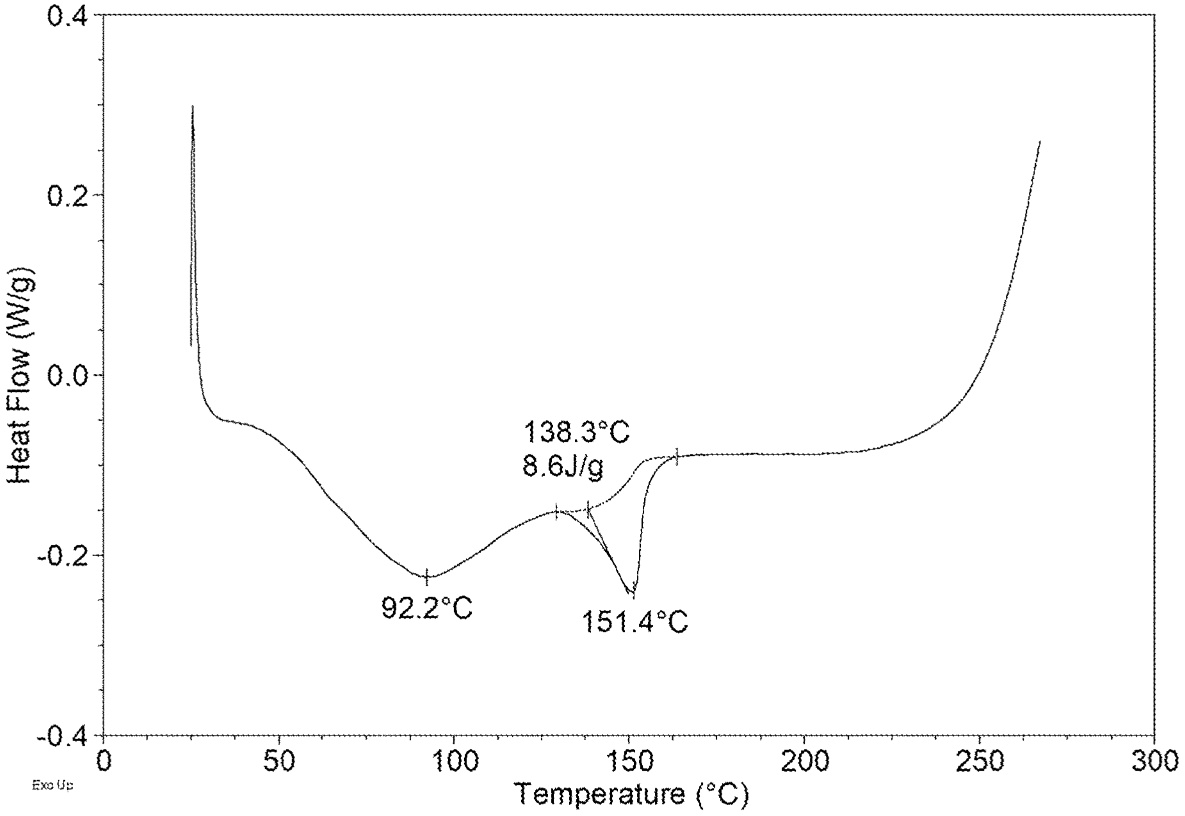
FIG. 21 provides a DSC thermogram of the crystalline mesylate salt of Compound I (form G), according to the examples.

The crystalline compounds may be characterized thermally. In any embodiment, the crystalline free base (form A) may have a DSC thermogram showing an onset of an endotherm at about 212.9° C. In any embodiment, the crystalline free base may have a DSC thermogram substantially as shown in FIG. 3. In any embodiment, the crystalline hydrochloride salt (form B) may have a DSC thermogram showing an onset of an endotherm at about 101.1° C. and/or about 184° C. In any embodiment, the crystalline hydrochloride salt may have a DSC thermogram substantially as shown in FIG. 8. In any embodiment, the crystalline hydrobromide salt (form D) may have a DSC thermogram showing an onset of an endotherm at about 110.3° C. and/or about 210.9° C. In any embodiment, the crystalline hydrobromide salt may have a DSC thermogram substantially as shown in FIG. 13. In any embodiment, the crystalline edisylate salt (form F) may have a DSC thermogram showing an onset of an endotherm at about 120.9° C. and/or about 204.1° C. In any embodiment, the crystalline edisylate salt may have a DSC thermogram substantially as shown in FIG. 18. In any embodiment, the crystalline mesylate salt (form G) may have a DSC thermogram showing an onset of an endotherm at about 92.2° C. and/or about 138.3° C. In any embodiment, the crystalline mesylate salt may have a DSC thermogram substantially as shown in FIG. 21.

Figure 2:
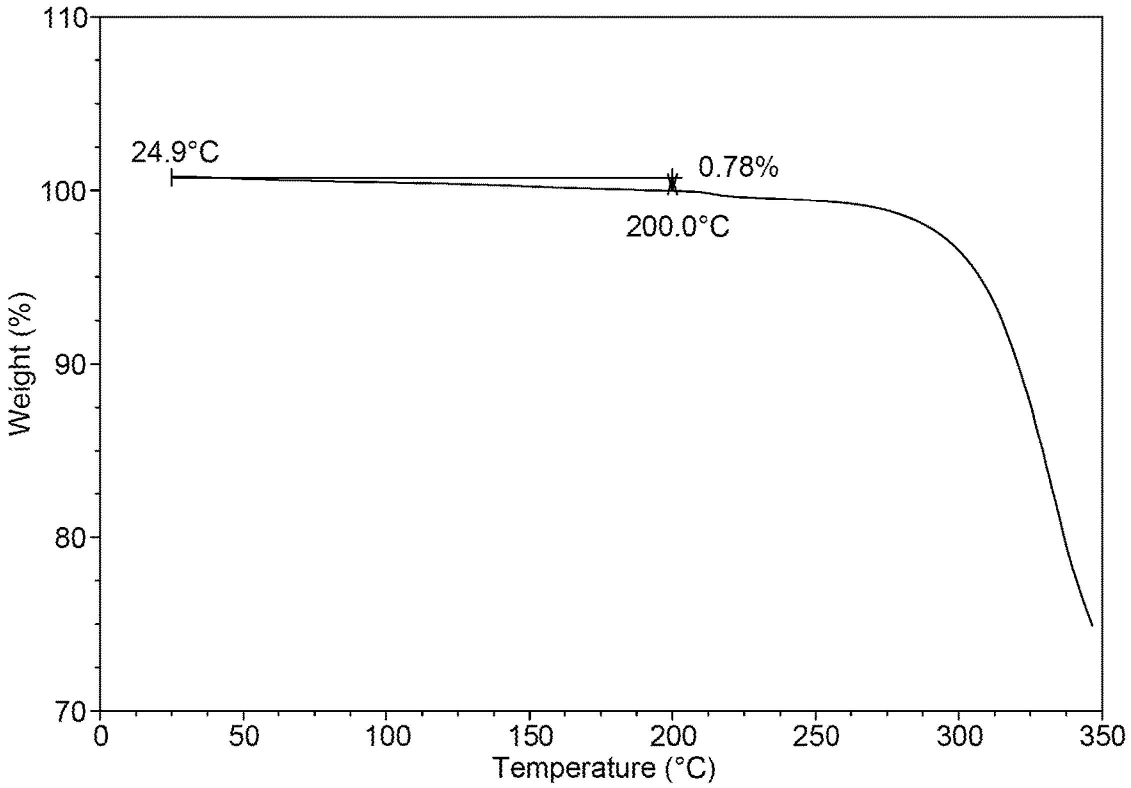
FIG. 2 provides a thermogravimetric analysis (TGA) thermogram of the crystalline free base of Compound I (form A), according to the examples.
Figure 7:
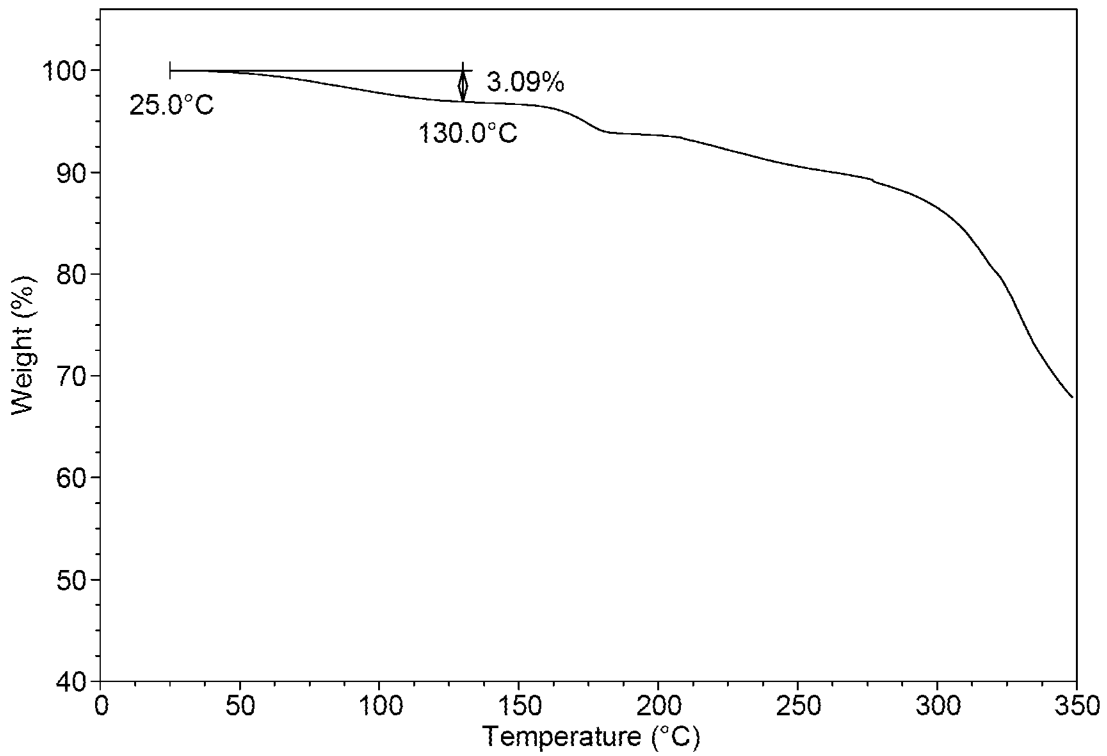
FIG. 7 provides a TGA thermogram of the crystalline hydrochloride salt of Compound I (form B), according to the examples.
Figure 12:
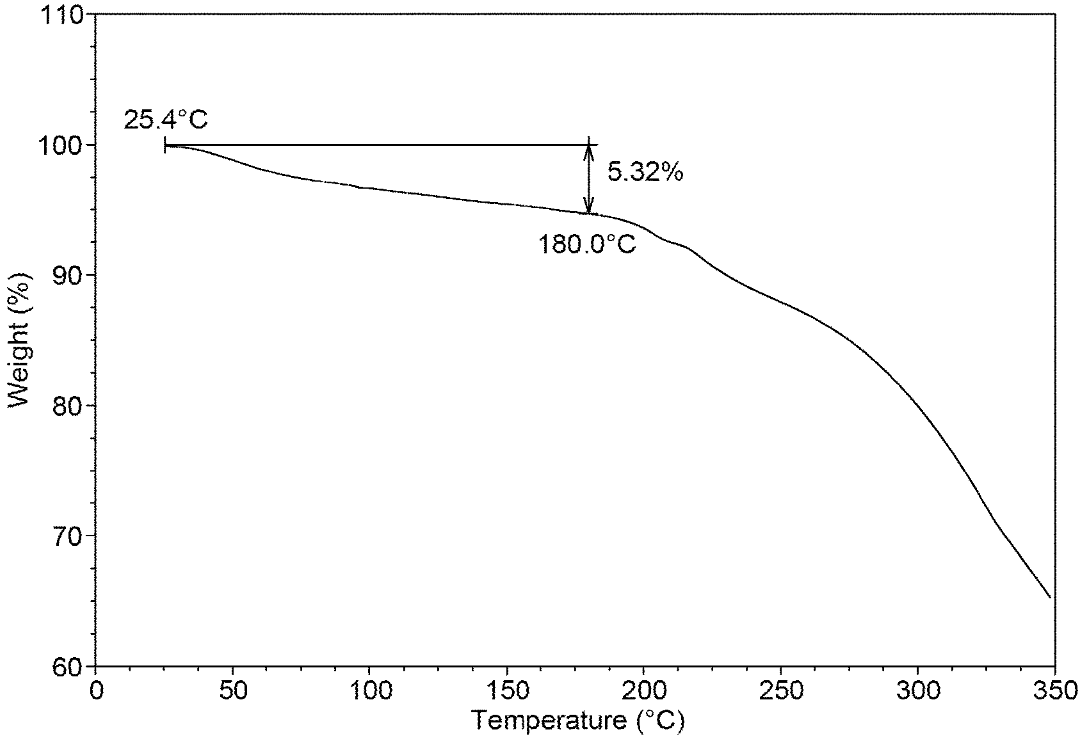
FIG. 12 provides a TGA thermogram of the crystalline hydrobromide salt of Compound I (form D), according to the examples.
Figure 17:
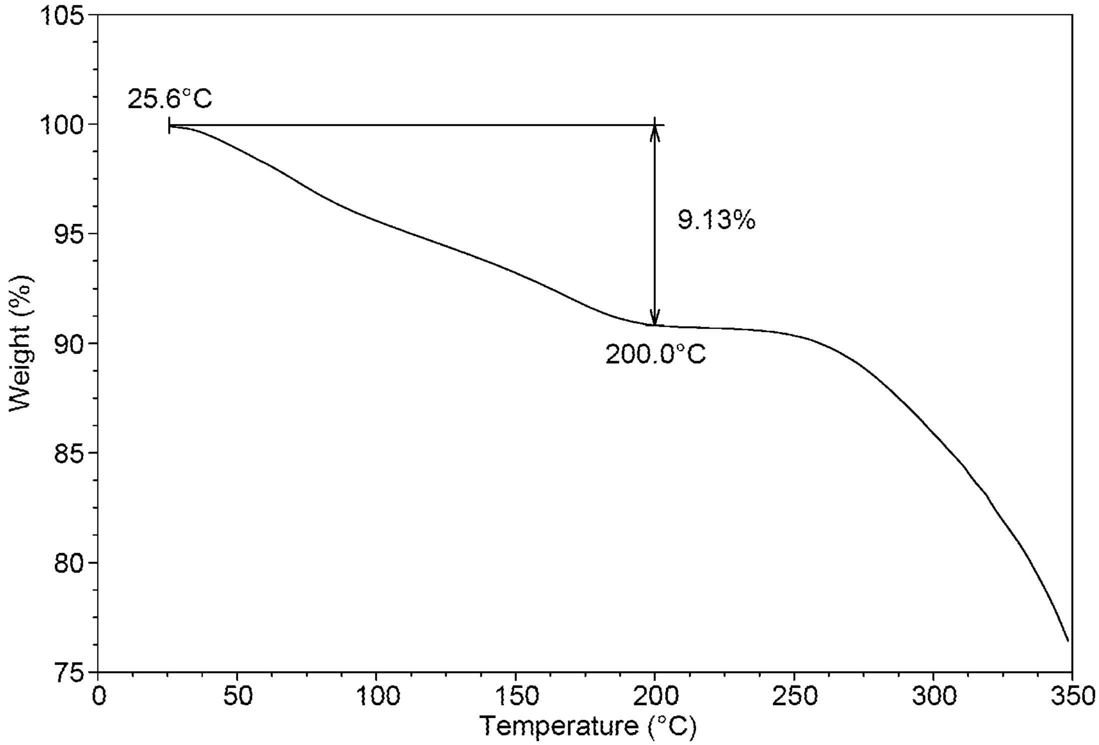
FIG. 17 provides a TGA thermogram of the crystalline edisylate salt of Compound I (form F), according to the examples.
Figure 20:
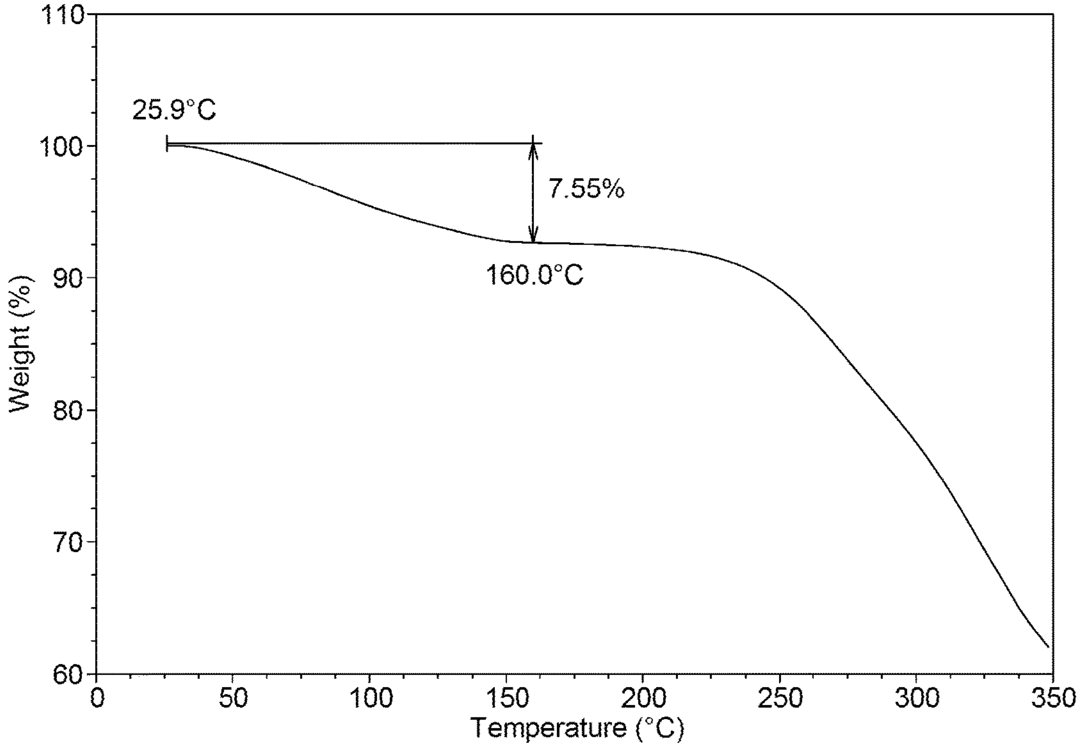
FIG. 20 provides a TGA thermogram of the crystalline mesylate salt of Compound I (form G), according to the examples.

The crystalline compounds may be characterized thermally. In any embodiment, the crystalline free base (form A) may have a TGA thermogram demonstrating a weight loss of about 0.8% (up to about 200° C.). In any embodiment, the crystalline free base may have a TGA thermogram substantially as shown in FIG. 2. In any embodiment, the crystalline hydrochloride salt (form B) may have a TGA thermogram demonstrating a weight loss of about 3.1% (up to about 130° C.). In any embodiment, the crystalline hydrochloride salt may have a TGA thermogram substantially as shown in FIG. 7. In any embodiment, the crystalline hydrobromide salt (form D) may have a TGA thermogram demonstrating a weight loss of about 5.3% (up to about 180° C.). In any embodiment, the crystalline hydrobromide salt may have a TGA thermogram substantially as shown in FIG. 12. In any embodiment, the crystalline edisylate salt (form F) may have a TGA thermogram demonstrating a weight loss of about 9.1% (up to about 200° C.). In any embodiment, the crystalline edisylate salt may have a TGA thermogram substantially as shown in FIG. 17. In any embodiment, the crystalline mesylate salt (form G) may have a TGA thermogram demonstrating a weight loss of about 7.6% (up to about 160° C.). In any embodiment, the crystalline mesylate salt may have a TGA thermogram substantially as shown in FIG. 20.

In any embodiment, the crystalline compound of Compound I (including any one of forms A-G) may have an XRPD including one, two, three, four, five, six, seven, eight, nine, or ten characteristic peaks, in terms of 2θ.

In some embodiments, the crystalline compound of Compound I (including any one of forms A-G) may be anhydrous. In any embodiment, the crystalline free base (form A) may be anhydrous. In any embodiment, the crystalline hydrochloride salt of form C may be anhydrous. In any embodiment, the crystalline hydrobromide salt of form E may be anhydrous.

In some embodiments, the crystalline compound of Compound I (including any one of forms A-G) may be a hydrate. In any embodiment, the crystalline hydrochloride salt of form B may be a hydrate (e.g., a monohydrate). In any embodiment, the crystalline hydrobromide salt of form D may be a hydrate (e.g., a dihydrate).

In some embodiments, the crystalline compound of Compound I (including any one of forms A-G) may be a solvate. In any embodiment, the crystalline edisylate salt of form F may be a 4-methyl-2-pentanone ("MIBK") solvate. In any embodiment, the crystalline mesylate salt of form G may be an ethyl acetate ("EtOAc") solvate.

As used herein, with respect to values of 2θ, the terms "about" and "substantially" indicate that such values for individual peaks can vary by ±0.4°. In some embodiments, the values of 2θ for individual peaks can vary by ±0.3°. In some embodiments, the values of 2θ for individual peaks can vary by ±0.2°.

As used herein, with respect to features such as endotherms, exotherms, baseline shifts, etc., the terms "about" and "substantially" indicate that their values can vary ±2° C. For DSC, variation in the temperatures observed will depend upon the rate of temperature change as well as sample preparation technique and the particular instrument employed. Thus, the values reported herein relating to DSC thermograms can vary ±4° C. For TGA, variation in the temperatures observed will depend upon the rate of temperature change as well as sample preparation technique and the particular instrument employed. Thus, the values reported herein relating to TGA thermograms can vary ±4° C.

As used herein, other than with respect to values of 2θ, endotherms, exotherms, and baseline shifts as defined above, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In addition to the techniques described above for characterizing crystalline forms of as described herein, XRPD, single crystal X-ray diffraction, DSC, dynamic vapor sorption (DVS), crystal morphology, solid state nuclear magnetic resonance, Raman scattering, infrared (IR) spectroscopy, and/or polarized light microscopy (PLM) may also be useful for characterization of other crystalline or amorphous forms of the present technology.

In another aspect, the present technology provides a method of making the crystalline compounds of Compound I disclosed herein.

In one embodiment, the crystalline free base of Compound I (form A) may be provided by contacting amorphous Compound I with seed of form A. In any embodiment, seeded composition is cooled. In any embodiment, n-heptane is added to the cooled composition. In any embodiment, the method may further include filtering the precipitate. In any embodiment, the method may further include drying the precipitate. In any embodiment, the seeded composition may be cooled to below about 35° C. (e.g., between about 10° C. to about 30° C.). In any embodiment, the seeded composition is cooled for about 2 to about 8 hours.

In another embodiment, the crystalline free base of Compound I (form A) may be provided by contacting amorphous Compound I with an organic solvent. In any embodiment, the organic solvent may include isopropanol, n-heptane, EtOAc, or a combination of two or more thereof. In any embodiment, the organic solvent may include isopropanol or EtOAc. In any embodiment, the method may further include filtering the precipitate. In any embodiment, the method may further include drying the precipitate. In any embodiment, the contacting occurs at room temperature (i.e., between about 20° C. to about 25° C.). In any embodiment, the contacting occurs for about 1 h to about 7 days, about 3 days to about 7 days, about 2 hours to about 14 hours, about 2 h to about 10 h, or about 2 hours to about 5 hours.

In any embodiment, the crystalline hydrochloride salt of Compound I (form B) may be provided by contacting a suspension of form A with hydrochloric acid ("HCl") to precipitate the crystalline hydrochloride salt. In any embodiment, the suspension of form A may include EtOAc. In any embodiment, the method may further include filtering the precipitate. In any embodiment, the method may further include drying the precipitate. In any embodiment, the method may further include contacting the precipitate with acetonitrile ("ACN") and/or water.

In any embodiment, the crystalline hydrochloride salt of Compound I (form C) may be provided by purging form B with inert gas (e.g., $N_2$). In any embodiment, the purging may be at about 20° C. to about 40° C. for about 10 minutes to about 30 minutes.

In any embodiment, the crystalline hydrobromide salt of Compound I (form D) may be provided by contacting a suspension of form A with hydrobromic acid ("HBr") to precipitate the crystalline hydrobromide salt. In any embodiment, the suspension of form A may include MIBK, n-heptane, or a combination thereof.

In any embodiment, the crystalline hydrobromide salt of Compound I (form E) may be provided by purging form D with inert gas (e.g., $N_2$). In any embodiment, the purging may be at about 20° C. to about 40° C. for about 10 minutes to about 30 minutes.

In any embodiment, the crystalline edisylate salt of Compound I (form F) may be provided by contacting a suspension of form A with ethanedisulfonic acid ("EDSA") to precipitate the crystalline edisylate salt. In any embodiment, the suspension of form A may include MIBK, n-heptane, or a combination thereof.

In any embodiment, the crystalline mesylate salt of Compound I (form G) may be provided by contacting a suspension of form A with methanesulfonic acid ("MSA") to precipitate the crystalline mesylate salt. In any embodiment, the suspension of form A may include EtOAc.

In any embodiment, the HCl, HBr, EDSA, or MSA used to contact form A may be present in an amount from about 1 equivalent to about 10 equivalents, from about 2 equivalents to about 9 equivalents, from about 3 equivalents to about 8 equivalents, from about 4 equivalents to about 7 equivalents, from about 1 equivalents to about 5 equivalents, from about 1 equivalents to about 3 equivalents, or from about 3 equivalents to about 6 equivalents, with respect to the molar amount of the form A contacted.

In any embodiment, the suspension of form A and the HCl, HBr, EDSA, or MSA are reacted or contacted from about 2 h to about 120 h, from about 12 h to about 110 h, or from about 24 h to about 96 h. In any embodiment, the suspension of form A and the HCl, HBr, EDSA, or MSA are reacted at room temperature.

In any embodiment, the crystals may be further subjected to steps such as, e.g., drying, purification, etc. In any embodiment, the crystals may be filtered. In any embodiment, the crystals may be subjected to drying at a suitable temperature. In one embodiment, the crystals may be dried at a temperature in the range of about 20° C. to about 60° C. In some embodiments, the crystals may be dried at a temperature in the range of about 20° C. to about 25° C. In some embodiments, the crystals may be dried at a temperature in the range of about 35° C. to about 55° C. In some embodiments, the crystals may be dried under reduced pressure in the range, for example, of about 10 mbar-about 40 mbar. The drying step may be conducted for a suitable period of time. Thus in one embodiment, the crystals are dried for a period of about 1 to about 72 hours, from about 2 to about 36 hours or from about 4 to about 18 hours. In some embodiments, the crystals are dried for about 48 h.

Crystalline forms as described herein may be isolated in substantially pure form. By "substantially pure" it is meant that more than 50% by weight of Compound I is present in one of the crystalline forms disclosed herein. In some embodiments of the isolated or substantially pure crystalline forms as described herein, Compound I may be present at least about 60%, at least about 70%, at least about 80%, at least about 90%, at least about 95%, at least about 97%, at least about 98%, or at least about 99% by weight of the indicated form. For example, in certain embodiments, the present technology provides crystals wherein at least about 50%, at least about 70%, at least about 80%, at least about 90%, at least about 95%, at least about 97%, at least about 98%, or at least about 99% by weight may be the crystal present as form A, form B, form D, form F, or form G.

The present technology also provides a pharmaceutical composition, which includes an effective amount of one or more of the crystalline forms as described herein for treating an FXR-mediated disorder or condition. The FXR-mediated disorder or condition may be hepatitis B, liver disease, hyperlipidemia, hypercholesteremia, obesity, metabolic syndrome, cardiovascular disease, gastrointestinal disease, atherosclerosis, or renal disease. For example, the disorder or condition may be a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

In a further related aspect, a method is provided that includes administering an effective amount of one or more of the crystalline forms as described herein or administering a pharmaceutical composition comprising an effective amount of one or more of the crystalline forms as described herein to a subject suffering from an FXR-mediated disorder or condition. The FXR-mediated disorder or condition may be hepatitis B, liver disease, hyperlipidemia, hypercholesteremia, obesity, metabolic syndrome, cardiovascular disease, gastrointestinal disease, atherosclerosis, or renal disease. In some embodiments, the disorder or condition is the disorder or condition may be a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

"Effective amount" refers to the amount of a crystalline form as described herein or compositions thereof as described herein required to produce a desired effect. One example of an effective amount includes amounts or dosages that yield acceptable toxicity and bioavailability levels for therapeutic (pharmaceutical) use including, but not limited to, the treatment of hyperlipidemia. Another example of an effective amount includes amounts or dosages that are capable of reducing symptoms associated with metabolic syndrome, such as, for example, obesity and/or metabolic syndrome. The effective amount of the crystalline form as described herein may selectively modulate FXR. As used herein, a "subject" or "patient" is a mammal, such as a cat, dog, rodent or primate. Typically, the subject is a human, and, preferably, a human suffering from or suspected of suffering from an FXR-mediated disorder or condition. The term "subject" and "patient" can be used interchangeably.

In still another aspect, the present technology provides methods of modulating FXR by contacting FXR with an effective amount of one or more of the crystalline forms as described herein.

Thus, the instant present technology provides pharmaceutical compositions and medicaments comprising any of the crystalline forms disclosed herein (e.g., forms A-G) and a pharmaceutically acceptable carrier or one or more excipients or fillers. The compositions may be used in the methods and treatments described herein. Such compositions and medicaments include a therapeutically effective amount of one or more of the crystalline forms as described herein. The pharmaceutical composition may be packaged in unit dosage form.

The pharmaceutical compositions and medicaments may be prepared by mixing one or more the crystalline forms disclosed herein with pharmaceutically acceptable carriers, excipients, binders, diluents or the like to prevent and treat disorders associated with the effects of increased plasma and/or hepatic lipid levels. The one or more crystalline forms disclosed herein and compositions thereof as described herein may be used to prepare formulations and medicaments that prevent or treat a variety of disorders associated with or mediated by FXR, including but not limited to hepatitis B, liver disease, hyperlipidemia, hypercholesteremia, obesity, metabolic syndrome, cardiovascular disease, gastrointestinal disease, atherosclerosis and renal disease. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more crystalline forms disclosed herein with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions, which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Crystalline forms of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of crystalline forms of the present technology by inhalation.

Dosage forms for the topical (including buccal and sublingual) or transdermal administration of one or more crystalline forms disclosed herein include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the one or more crystalline forms disclosed herein across the skin. The rate of such flux can be controlled by either providing a rate controlling membrane (e.g., as part of a transdermal patch) or dispersing the one or more crystalline forms disclosed herein in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering one or more crystalline forms disclosed herein to a patient in increasing amounts until for example, (for metabolic syndrome and/or obesity) the elevated plasma or elevated white blood cell count or hepatic cholesterol or triglycerides or progression of the disease state is reduced or stopped. For metabolic syndrome and/or obesity, the progression of the disease state can be assessed using in vivo imaging, as described, or by taking a tissue sample from a patient and observing the target of interest therein.

The one or more crystalline forms disclosed herein can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of hyperlipidemia, such as, for example, a decrease in triglycerides in the blood stream. Effectiveness of the compositions and methods of the present technology may also be demonstrated by a decrease in the signs and symptoms of hepatitis B, liver disease, hyperlipidemia, hypercholesteremia, obesity, metabolic syndrome, cardiovascular disease, gastrointestinal disease, atherosclerosis, or renal disease.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The one or more crystalline forms disclosed herein can also be administered to a patient along with other conventional therapeutic agents that may be useful in the treatment of hepatitis B, liver disease, hyperlipidemia, hypercholesteremia, obesity, metabolic syndrome, cardiovascular disease, gastrointestinal disease, atherosclerosis, or renal disease. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially be effective for the treatment of hepatitis B, liver disease, hyperlipidemia, hypercholesteremia, obesity, metabolic syndrome, cardiovascular disease, gastrointestinal disease, atherosclerosis, or renal disease.

In one aspect, one or more crystalline forms disclosed herein may be administered to a patient in an amount or dosage suitable for therapeutic use. Generally, a unit dosage comprising one or more the crystalline forms of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

A crystalline forms of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled crystalline form of the present technology. A detectable or imaging effective quantity is a quantity of a labeled crystal of the present technology necessary to be detected by the detection method chosen. For example, a detectable quantity can be an administered amount sufficient to enable detection of binding of the labeled compound to a target of interest including, but not limited to, a KOR. Suitable labels are known by those skilled in the art and can include, for example, radioisotopes, radionuclides, isotopes, fluorescent groups, biotin (in conjunction with streptavidin complexation), and chemiluminescent groups. Upon binding of the labeled crystal to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, crystalline forms of the present technology can bind to or interact with a target of interest or precursors, portions, fragments and peptides thereof and/or their deposits.

Treatment within the context of the instant technology, means an alleviation, in whole or in part, of symptoms associated with a disorder or disease, or slowing or halting of further progression or worsening of those symptoms, or tending to prevent or ward off the disease or disorder in a subject at risk for developing the disease or disorder.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

The present technology, thus generally described, will be understood more readily by reference to the following examples, which are provided by way of illustration and are not intended to be limiting of the present technology.

EXAMPLES

The following abbreviations are used throughout the present disclosure with respect to chemical and biological terminology:

DCM: Dichloromethane
DMSO: Dimethylsulfoxide
ACN: Acetonitrile
THF: Tetrahydrofuran
2-MeTHF: 2-Methyltetrahydrofuran
AcOH: Acetic acid
CPME: Cyclopentyl methyl ether
DIBAL-H: Diisobutylaluminum hydride
DIEA: N,N-diisopropylethylamine
DMF: Dimethylformamide
EtOAc: Ethyl acetate
Hep: Heptane
IPAc: Isopropyl acetate MIBK: 4-Methyl-2-pentanone
MTBE: t-Butyl methyl ether
NCS: N-Chlorosuccinimide
IPA: Isopropanol
MeOH: Methanol
DSC: Differential scanning calorimetry
DVS: Dynamic vapor sorption
ESI-MS: Electrospray ionization-mass spectroscopy
FT-IR: Fourier transform-infrared
HPLC: High performance liquid chromatography
M: Molar
NMR: Nuclear magnetic resonance spectroscopy
RH: Relative humidity
RT: Room temperature
SEM: Scanning electron microscopy
TGA: Thermo gravimetric analysis
UV: Ultraviolet
XRPD: X-ray powder diffraction
PLM: Polarized light microscopy General Methods, Instruments, and Standards Employed X-Ray Powder Diffraction (XRPD)

XRPD analysis was conducted with a PANalytical Empyrean and X'Pert[3] X-ray powder diffract meter. The XRPD parameters used are provided in Table 1.

TABLE 1

Parameters for XRPD analysis

| Parameters | X' Pert[3] | Empyrean |
|---|---|---|
| X-Ray wavelength | Cu, kα; Kα1 (Å): 1.540598, Kα2 (Å): 1.544426 intensity ratio Kα2/Kα1: 0.50 | Cu, kα; Kα1 (Å): 1.540598, Kα2 (Å): 1.544426 intensity ratio Kα2/Kα1: 0.50 |
| X-Ray tube setting | 45 kV, 40 mA | 45 kV, 40 mA |
| Divergence slit | 1/8° | Automatic |
| Scan mode | Continuous | Continuous |
| Scan range (°2TH) | 3°~40° | 3°~40° |
| Step size (°2TH) | 0.0263 | 0.0167 |
| Counting time (s) | 46.665 | 33.020 |
| Test time (s) | ~5 min | ~10 min |

Thermogravimetric Analysis (TGA) and Differential Scanning Calorimetry (DSC)

TGA data was collected using a TA Q5000/Discovery 5500 TGA from TA Instruments. DSC was performed using a TA Q200/Q2000/Discovery 2500 DSC from TA Instruments. Detailed parameters used are provided in 2.

TABLE 2

Parameters for TGA and DSC test

| Parameters | TGA | DSC |
|---|---|---|
| Method | Ramp | Ramp |
| Sample pan | Aluminum, open | Aluminum, crimped |
| Temperature | RT-350° C. | 25-270° C. |
| Heating rate | 10° C./min | 10° C./min |
| Purge gas | $N_2$ | $N_2$ |

Proton Nuclear Magnetic Resonance ($^1$H NMR)

$^1$H solution NMR was collected on Bruker 400M NMR Spectrometer using DMSO-$d_6$.

High Performance Liquid Chromatography (HPLC)

Agilent 1260 HPLC was utilized and detailed chromatographic conditions are provided in Tables 3 and 4 for purity and solubility test, respectively.

TABLE 3

Chromatographic conditions and parameters for purity test

| | | |
|---|---|---|
| HPLC | Agilent 1260 with DAD detector | |
| Column | Waters Xbridge C18, 150 × 4.6 mm, 5 μm | |
| Mobile phase | A: 0.05% TFA in H2O<br>B: 0.05% TFA in ACN | |
| Gradient table | Time (min) | % B |
| | 0.0 | 10 |
| | 6.0 | 48 |
| | 10.5 | 48 |
| | 16.0 | 90 |
| | 20.5 | 90 |
| | 21.0 | 10 |
| | 26.0 | 10 |
| Run time | 26.0 min | |
| Post time | 0.0 min | |
| Flow rate | 1.0 mL/min | |
| Injection volume | 5 μL | |
| Detector wavelength | UV at 225 nm | |
| Column temperature | 35° C. | |
| Sampler temperature | RT | |
| Diluent | MeOH | |

TABLE 4

Chromatographic conditions and parameters for solubility test

| | | |
|---|---|---|
| HPLC | Agilent 1260 with VWD detector | |
| Column | Waters Xbridge C18, 150 × 4.6 mm, 5 μm | |
| Mobile phase | A: 0.05% TFA in water<br>B: 0.05% TFA in ACN | |
| Gradient table | Time (min) | % B |
| | 0.0 | 10 |
| | 10.00 | 90 |
| | 12.00 | 90 |
| | 12.01 | 10 |
| | 15.00 | 10 |
| Run time | 15.0 min | |
| Post time | 0.0 min | |
| Flow rate | 1.0 mL/min | |
| Injection volume | 5 μL | |
| Detector wavelength | UV at 225 nm | |
| Column temperature | 35° C. | |
| Sampler temperature | RT | |
| Diluent | MeOH | |

Ion Chromatography (IC)

ThermoFisher ICS-1100 was utilized and detailed conditions are provided in Table 5.

TABLE 5

Ion chromatograph conditions and parameters

| | |
|---|---|
| IC | ThermoFisher ICS-1100 |
| Column | IonPac AS18 Analytical Column (4 × 250 mm) |
| Mobile phase | 25 mM NaOH |
| Injection volume | 25 μL |
| Flow rate | 1.0 mL/min |
| Cell temperature | 35° C. |
| Column temperature | 35° C. |
| Current | 80 mA |
| Run time | 6.0 min for $Cl^-$, 12.0 min for $Br^-$ |

Dynamic Vapor Sorption (DVS)

DVS was measured via a SMS (Surface Measurement Systems) DVS Intrinsic. The relative humidity at 25° C. was calibrated against deliquescence point of LiCl, $Mg(NO_3)_2$ and KCl. Parameters for DVS test are provided in Table 6.

TABLE 6

| Parameters for DVS test | |
|---|---|
| Parameters | DVS |
| Temperature | 25° C. |
| Sample size | 20~40 mg |
| Gas and flow rate | N2, 200 mL/min |
| dm/dt | 0.002%/min |
| Min. dm/dt stability duration | 10 min |
| Max. equilibrium time | 180 min |
| RH range | 0% RH~95% RH~0% RH (Anhydrate)<br>Room humidity ~95% RH~0% RH~95% RH (Hydrate) |
| RH step size | 10% RH from 0% RH to 90% RH & 90% RH to 0% RH<br>5% RH from 90% RH to 95% RH & 95% RH to 90% RH |

Example 1: Preparation and Characterization of Form A of Compound I

Method 1. Isopropyl alcohol/n-heptane (1:1, v/v) (50 μL) was added to 15 mg of Compound I to obtain a suspension and magnetically stirred at room temperature for 5 days. The solid product was isolated by filtration.

Method 2. EtOAc (100 μL) was added to 40 mg of Compound I and magnetically stirred at room temperature for 4 hours. The solid product was isolated by filtration.

Method 3. Isopropyl alcohol (100 μL) was added to 40 mg of Compound I and magnetically stirred at room temperature for 4 hours. The solid product was isolated by filtration.

Method 4. Isopropyl alcohol (1.7 mL) was added to 300 mg of Compound I and magnetically stirred at room temperature overnight. The solid product was isolated by filtration.

Method 5. EtOAc (10 mL) was added to 6 g of Compound I and magnetically stirred at room temperature for 3 hours. The solid product was isolated by filtration.

Method 6. To a solution of 3A (methyl(R)-2-(4-((5-cyclopropyl-3-(2,6-dichlorophenyl)isoxazol-4-yl)methyl)-2-methylpiperazin-1-yl)-4-methoxybenzo[d]thiazole-6-carboxylate of which the synthetic procedure was shown below) (6.30 kg, 1.0 eq.) in MeOH (1.6 L, 0.25 V), THF (12.6 L, 2 V), and water (12.6 L, 2 V) were added NaOH (2.1 kg, 5.0 eq.) at 15±10° C. The resulting mixture was stirred for 10 h at 50±5° C. LC showed 3A=0%. The temperature was adjusted to 20±10° C. and water (4 V) was added to the reaction mixture followed by HCl aq. (4 M, 5.3 eq.) at 20±10° C. Next, ethyl acetate (7 V) was added and the mixture was stirred for 20 minutes. After a phase separation, the organic layer was washed with water (2 V*3). The organic layer was concentrated to 5-6 V at 70±10° C. Additional EtOAc (2 V each time) was added and azeotropic distillation was continued until tested water content (KF) was ≤0.23%. Seed of Form A of Compound I (0.5%, w/w %) was added to the solution at 70±10° C. The mixture was cooled to 20±10° C. within at least 5 hours followed by the addition of n-Heptane (5 V) and stirring for 2 h. The solid product was isolated by filtration and dried at 45±10° C. to give 5.76 kg compound I (purity: 99.7%, LCMS (ESI, m/z): $[M+H]^+$=573.2).

The synthetic procedure of 3A

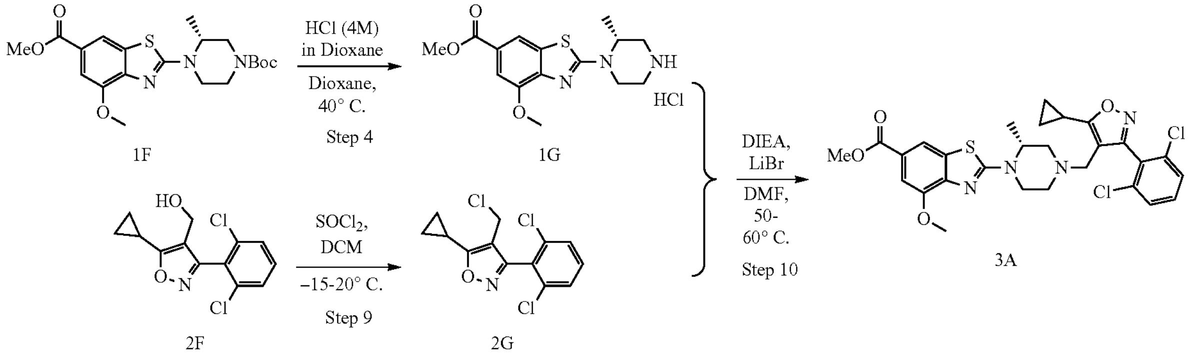

1F 1G 2F 2G 3A

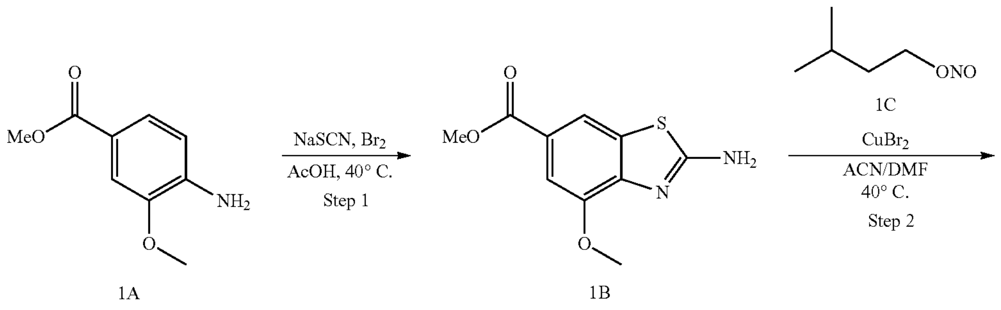

1A 1B 1C

-continued

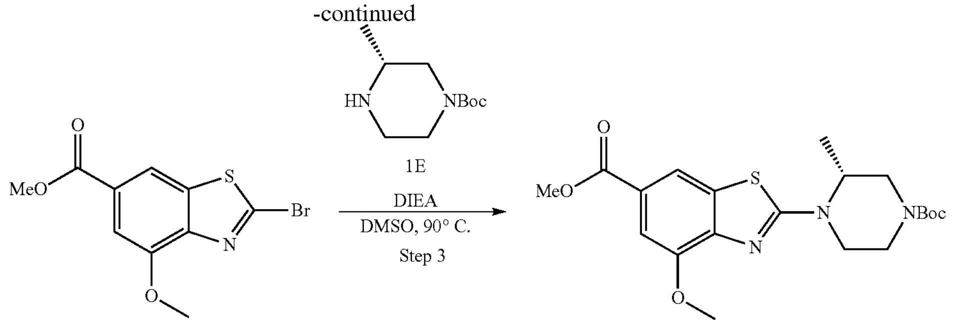

1D 1F

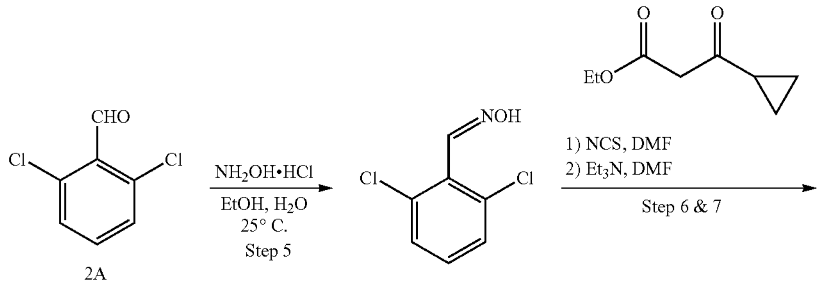

2A 2B

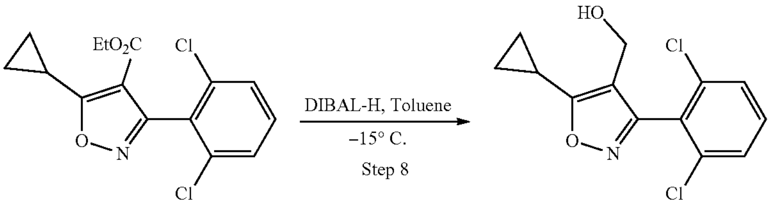

2E 2F

Step 1. To a stirring mixture of 1A (6.0 kg, 1.0 eq.), NaSCN (5.91 kg, 2.2 eq.) in AcOH (78 L, 13 V) was added $Br_2$ (6.35 kg, 1.2 eq.) dropwise at 40° C. (Control temp. 40-50° C.). The resulting mixture was stirred for 12 h at 40° C. LC showed 1A=0%. The mixture was cooled to room temperature. The precipitate was filtered and washed with MTBE. The solid was slurried in water (10 V), the pH was adjusted to about 8 to about 9 with aq. $NH_4OH$, and stirred for 2 h. The solid was filtered and dried at 45° C. to get the product (1B) 6.62 kg, yield: 84%, purity: 99%, KF=0.02%. LCMS (ESI, m/z): $[M+H]^+$=239.0. $^1H$ NMR (300 MHz, DMSO-$d_6$) δ7.95 (d, J=1.5 Hz, 1H), 7.85 (s, 2H), 7.35 (d, J=1.6 Hz, 1H), 3.88 (s, 3H), 3.83 (s, 3H).

Step 2. To a solution of 1B (6.0 kg, 1.0 eq.), $CuBr_2$ (8.87 kg, 1.57 eq.) in ACN (50.4 L, 8.4 V) and DMF (9.6 L, 1.6 V) was added 1C (4.27 kg, 1.44 eq.) dropwise at 40° C. (control temp. 40-50° C.). The resulting mixture was stirred for 2 h at 40° C. LC showed 1B=0%. The mixture was cooled to 15° C. The water (36.3 L, 11 V) was added to reaction mixture slowly to crystallize (control temp.<25° C.). The precipitate was filtered, washed with ACN: $H_2O$=1:2 (3.3 L*2), $H_2O$ (3.3 L*2). The solid was dried at 40° C. to give the crude product (1D). The crude product (13.4 kg) was dissolved in DCM (187 L, 14 V) at 30° C. to give a suspension. The precipitate was filtered and washed with DCM (13.4 L, 1 V). The organic layer was concentrated to 2.5 V, 33.5 L. The heptane (67 L, 5 V) was added to the above organic layer slowly to crystallize (control temp.<25° C.). The precipitate was filtered. The solid was dried at 40° C. to give the crude product 9.862 kg, yield: 52.7%, purity: 97.9%, KF=0.1%. LCMS (ESI, m/z): $[M+H]^+$=301.9.

Step 3. To a solution of 1D (4.9 kg, 1.0 eq.), 1E (3.9 kg, 1.2 eq.) in DMSO (24.5 L, 5 V) was added DIEA (4.19 kg, 2 eq.) at 25±5° C. The resulting mixture was stirred for 20 h at 90° C. LC showed 1D=0.5% (area %<0.6%). The mixture was cooled to 50° C. The DMSO (24.5 L, 5 V) was added to reaction mixture. The water (49 L, 10 V) was added to reaction mixture slowly to crystallize (control temp.<50° C.) and stirred for 1 h at 20° C. The precipitate was filtered and washed with DMSO: $H_2O$=1:2 (2 V*2), $H_2O$ (2 V*2). The solid was dried at 40° C. to give the crude product (1F) 8.5 kg, 97.3%. The crude product (8.5 kg) was dissolved in DCM (25.5 L, 3 V) at reflux to give a clear solution. The heptane (76 L, 9 V) was added to the above organic layer slowly to crystallize. The mixture was cooled to 20° C. and stirred for 12 h. The precipitate was filtered and washed with Hep.: DCM=5:1 (2 V*2). The solid was dried at 40° C. to give the product 5.44 kg, Yield: 79.5%, purity: 99%, KF=0.14%. LCMS (ESI, m/z): $[M+H]^+$=422.2. $^1H$ NMR (300 MHz, Chloroform-d) δ7.98 (s, 1H), 7.50 (s, 1H), 4.28 (s, 2H), 3.98 (d, J=32.9 Hz, 9H), 3.44 (td, J=12.7, 3.7 Hz, 1H), 3.08 (m, 2H), 1.49 (s, 9H), 1.31 (d, J=6.7 Hz, 3H).

Step 4. To a solution of 1F (7.0 kg, 1.0 eq.) in 1,4-dioxane (21 L, 3 V) was added 4 M HCl in 1,4-dioxane (42 L, 6 V) at 25±5° C. The resulting mixture was stirred for 4 h at 40±5° C. to generate a precipitate. LC showed 1F=0% (area % of 1F≤0.2%). Adjust temp. to 25±5° C. The solid was filtered and washed with MTBE (2 V*2). The solid was dried at 40±5° C. to give the product 6.25 kg, purity: 99.8%, assay (Q-NMR): 69.5%, KF=2.4%. LCMS (ESI, m/z): $[M+H]^+$=322.2. $^1$H NMR (300 MHz, DMSO-$d_6$) δ9.96 (m, 1H), 9.52 (s, 1H), 8.11 (d, J=1.5 Hz, 1H), 7.41 (d, J=1.5 Hz, 1H), 4.52 (s, 1H), 4.07 (d, J=14.0 Hz, 1H), 3.92 (s, 3H), 3.85 (s, 3H), 3.52 (m, 1H), 3.27 (m, 2H), 3.07 (m, 1H), 1.43 (d, J=7.0 Hz, 3H).

Step 5. To a solution of 2A (3.0 kg, 1 eq.) in EtOH (21 L, 7 V) was added $H_2O$ (21 L, 7 V) followed by the addition of $NH_2OH$ HC (1.31 kg, 1.1 eq.) in batches at 25° C. The resulting mixture was stirred for 2 h at 25° C. LC showed 2A=0.43% (area %<1%). Water (1 V) was added, and stirred for 1 h, the precipitate was filtered, and washed with $H_2O$:EtOH=4:1 (1 V*2), aq. $NaHCO_3$ (1 V, 2% w/w), water (2 V*2). The solid was dried at 40° C. to get the product 2.90 kg, purity: 99%, yield: 89%, KF=0.01%. LCMS (ESI, m/z): $[M+H]^+$=223.1. $^1$H NMR (300 MHz, DMSO-$d_6$) δ11.80 (s, 1H), 8.23 (s, 1H), 7.60-7.51 (m, 2H), 7.43 (dd, J=8.9, 7.1 Hz, 1H).

Step 6. To a solution of 2B (4.6 kg, 1.0 eq.) in DMF (13.8 L, 3 V) was added NCS (3.42 kg, 1.1 eq.) in several batches at 30° C. (control temp.<40° C.). The resulting mixture was stirred for 5 h at 35° C. The mixture was cooled to room temperature. The reaction mixture was used directly without further purification.

Step 7. To a solution of 2D (4.15 kg, 1.1 eq.) and $Et_3N$ (6.12 kg, 2.5 eq.) in DMF (13.8 L, 3 V) was added a solution of above 2C at 15° C., then stirred at 20° C. for 36 h, LC showed 2C=0.58% (area %<1.5%). Then DMF (3 V) was added, water (7.7 V) was added slowly (control temp.<35° C.), and precipitate was generated. Stirred for 1 h, then filtered, washed the cake with water:DMF=2:1 (2 V), water (2 V), the solid was dried at 40° C. to obtain the product 6.55 kg, purity: 99%, yield: 82.9%, KF=0.02%. LCMS (ESI, m/z): $[M+H]^+$=326.0. $^1$H NMR (300 MHz, Chloroform-d) δ7.47-7.31 (m, 3H), 4.14 (q, J=7.1 Hz, 2H), 2.95 (tt, J=8.4, 5.1 Hz, 1H), 1.49-1.23 (m, 4H), 1.04 (t, J=7.1 Hz, 3H).

Step 8. To a solution of 2E (6.0 kg, 1.0 eq.) in toluene (18 L, 3 V) was added DIBAL-H (27 L, 2.2 eq.) dropwise at −15° C. (control temp.<0° C.). The resulting mixture was stirred for 12 h at −10° C. LC showed 2E-0% (area %<0.2%). To the mixture was added 2-Me-THF (30 L, 5 V), cooled to −20° C., and added HCl (34.8 L, 4 M) (control temp.<20° C.). The organic layer was separated and washed with water (18 L, 1 V*3). The organic layer was concentrated to (18 L, 3 V) to give a white solid. The precipitate was filtered and dried at 40° C. to get the product 3.5 kg, yield: 67%, purity: 99%, KF=0.08%. LCMS (ESI, m/z): $[M+H]^+$=384.0. $^1$H NMR (300 MHz, DMSO-$d_6$) δ7.68-7.50 (m, 3H), 4.95 (t, J=5.2 Hz, 1H), 4.22 (d, J=5.2 Hz, 2H), 2.34 (tt, J=8.3, 5.3 Hz, 1H), 1.11 (ddt, J=9.2, 7.6, 2.7 Hz, 4H).

Step 9. To a solution of 2F (8.35 kg, 1.0 eq.) in DCM (41.7 L, 5 V) was added $SOCl_2$ (3.7 kg, 1.06 eq.) dropwise at −20° C. (<−12° C.). The resulting mixture was stirred for 12 h at −15° C. LC showed 2F=0.19% (area %<0.2%). To the mixture was added water (3 V) (control temp.<5° C.). The organic layer was separated, concentrated, and dried to give the product 8.57 kg, yield: 96%, purity: 99%, KF=0.082%. LCMS (ESI, m/z): $[M+H]^+$=302.0. $^1$H NMR (300 MHz, Chloroform-d) δ7.51-7.33 (m, 3H), 4.38 (s, 2H), 2.16 (tt, J=8.4, 5.1 Hz, 1H), 1.38-1.14 (m, 4H).

Step 10. To a solution of 1G (6.0 kg, assay: 69.5%, 1.0 eq.), DIEA (11.76 kg, 6 eq.) in DMF (60 L, 10 V) was added LiBr (2.64 kg, 2.2 eq.), 2G (14.56 kg, 1.15 eq.) at 15±10° C. The resulting mixture was stirred for 38 h at 55±5° C. LC showed 1G=1.6%. The temperature was adjusted to 25±5° C. and water (10 V) was added to the reaction mixture slowly. The precipitate was stirred for 2 h. The solid was filtered and washed with water:DMF=2:1 (2 V*2), water (2 V*2), Hep. (2 V*2). The solid was dried at 40±5° C. to give the crude product. The crude product was dissolved in DMF (5 V) at 65±5° C., the solution was cooled to 15±5° C. slowly within 7 h, MeOH (10 V) was added slowly, the precipitate was stirred for 2 h. The solid was filtered and washed with MeOH:DMF=3:1 (2 V*2), MeOH (2 V*2). The solid was dried at 40±5° C. to give the product 6.53 kg, purity: 100%, yield: 85.65%, LOD=0.5%. LCMS (ESI, m/z): $[M+H]^+$=587.1. $^1$H NMR (300 MHz, Chloroform-d) δ7.97 (s, 1H), 7.52-7.33 (m, 4H), 4.14 (d, J=7.4 Hz, 1H), 3.98 (d, J=29.6 Hz, 7H), 3.32 (t, J=10.5 Hz, 3H), 2.90 (d, J=11.1 Hz, 1H), 2.62 (d, J=11.0 Hz, 1H), 2.41-1.84 (m, 3H), 1.40-0.74 (m, 7H).

Figure 1:
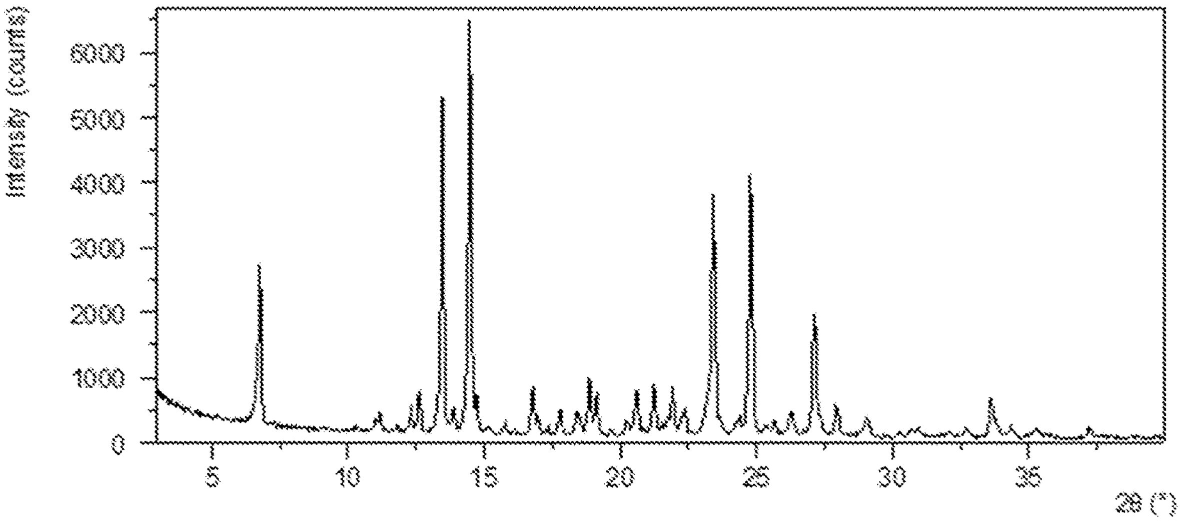
FIG. 1 provides an X-ray powder diffraction (XRPD) spectrum of the crystalline free base of Compound I (form A), according to the examples.

The solid samples from each method were analyzed by XRPD. The results showed consistent crystal forms (form A) were obtained by crystallization using isopropanol/n-heptane (method 1), EtOAc (methods 2 and 5), isopropanol (methods 3 and 4), and EtOAc/n-heptane (method 6). An XRPD of the crystalline form (form A) is shown in FIG. 1. Peaks from the XRPD pattern are listed in Table 7A.

TABLE 7A

XRPD data for Form A of Compound I

| No. | Pos. [°2θ] | d-spacing [Å] | Rel. Int. [%] |
|---|---|---|---|
| 1 | 6.77 | 13.06 | 37.69 |
| 2 | 11.17 | 7.92 | 4.63 |
| 3 | 12.32 | 7.19 | 5.40 |
| 4 | 12.63 | 7.01 | 9.82 |
| 5 | 13.48 | 6.57 | 86.67 |
| 6 | 13.88 | 6.38 | 5.85 |
| 7 | 14.48 | 6.12 | 100.00 |
| 8 | 14.75 | 6.01 | 9.14 |
| 9 | 15.76 | 5.62 | 1.95 |
| 10 | 16.79 | 5.28 | 11.58 |
| 11 | 16.99 | 5.22 | 4.42 |
| 12 | 17.32 | 5.12 | 1.46 |
| 13 | 17.79 | 4.99 | 5.66 |
| 14 | 18.42 | 4.82 | 5.44 |
| 15 | 18.89 | 4.70 | 14.05 |
| 16 | 19.14 | 4.64 | 9.84 |
| 17 | 19.69 | 4.51 | 1.02 |
| 18 | 20.24 | 4.39 | 3.49 |
| 19 | 20.63 | 4.31 | 11.12 |
| 20 | 21.24 | 4.18 | 12.86 |
| 21 | 21.93 | 4.05 | 11.83 |
| 22 | 22.38 | 3.97 | 5.98 |
| 23 | 23.42 | 3.80 | 59.22 |
| 24 | 24.32 | 3.66 | 3.60 |
| 25 | 24.77 | 3.59 | 64.04 |
| 26 | 25.66 | 3.47 | 3.79 |
| 27 | 26.29 | 3.39 | 5.89 |
| 28 | 27.12 | 3.29 | 29.88 |
| 29 | 27.92 | 3.20 | 7.92 |
| 30 | 29.09 | 3.07 | 5.05 |
| 31 | 30.24 | 2.96 | 1.11 |
| 32 | 30.66 | 2.92 | 2.03 |
| 33 | 32.70 | 2.74 | 2.29 |
| 34 | 33.60 | 2.67 | 10.39 |
| 35 | 34.38 | 2.61 | 2.54 |
| 36 | 35.28 | 2.54 | 2.24 |
| 37 | 37.20 | 2.42 | 2.65 |

TGA analysis of Form A of Compound I provided a weight loss of 0.8% up to 200° C. The TGA thermogram is provided in FIG. 2.

DSC analysis of Form A of Compound I provided one sharp endothermic peak with an onset temperature of 212.9° C., which is due to melting of material. The DSC thermogram is provided in FIG. 3.

Figure 4:
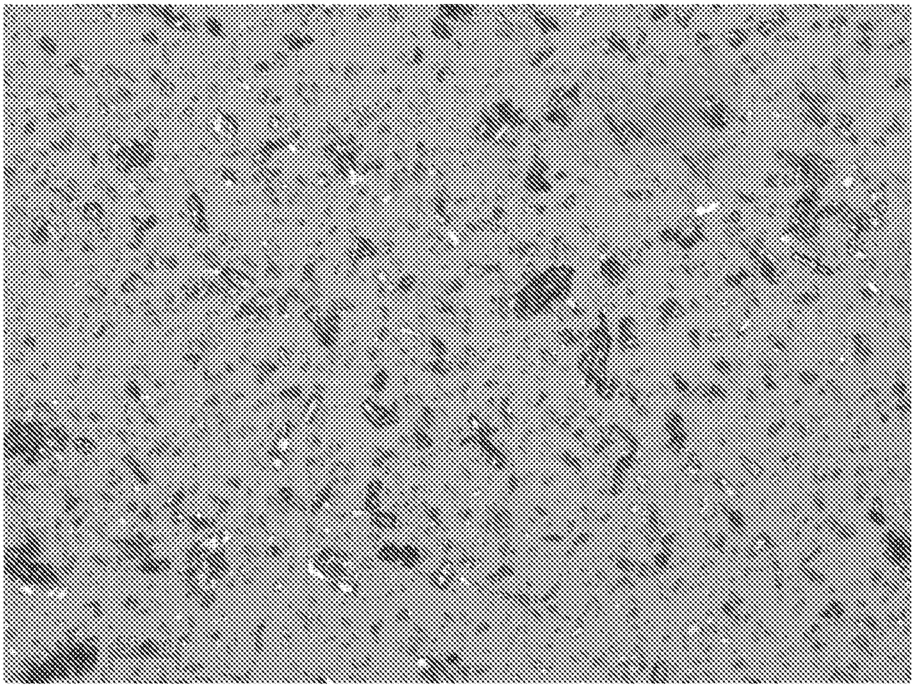
FIG. 4 provides a polarized light microscopy (PLM) image of the crystalline free base of Compound I (form A), according to the examples.

The PLM of Form A of Compound I provided irregular particles with birefringence. The PLM image is provided in FIG. 4.

Form A of Compound I was confirmed as an anhydrous, non-solvated crystalline form.

A sample of form A of Compound I was also tested for single crystal analysis. Preliminary examination and data collection were performed on a Rigaku XtaLAB Synergy R (CuKα radiation, λ=1.54184 Å) diffractometer and analyzed with the CrysAlisPro (Rigaku, V1.171.40.14e, 2018) software package. The structure was solved in the space group $P2_1$ with the $ShelXT_1$ structure solution program using Intrinsic Phasing and refined with $ShelXL_2$ (Version 2018/3) refinement package using fullmatrix least-squares on $F_2$ contained in OLEX2[3]. All non-hydrogen atoms were refined anisotropically. The hydrogen atoms (H1A and H1B) connected with the oxygen atoms (O1A and O2A) were determined and refined freely based on the Fourier Map. Other hydrogen atoms were calculated geometrically and refined using the riding model.

Figure 28A:
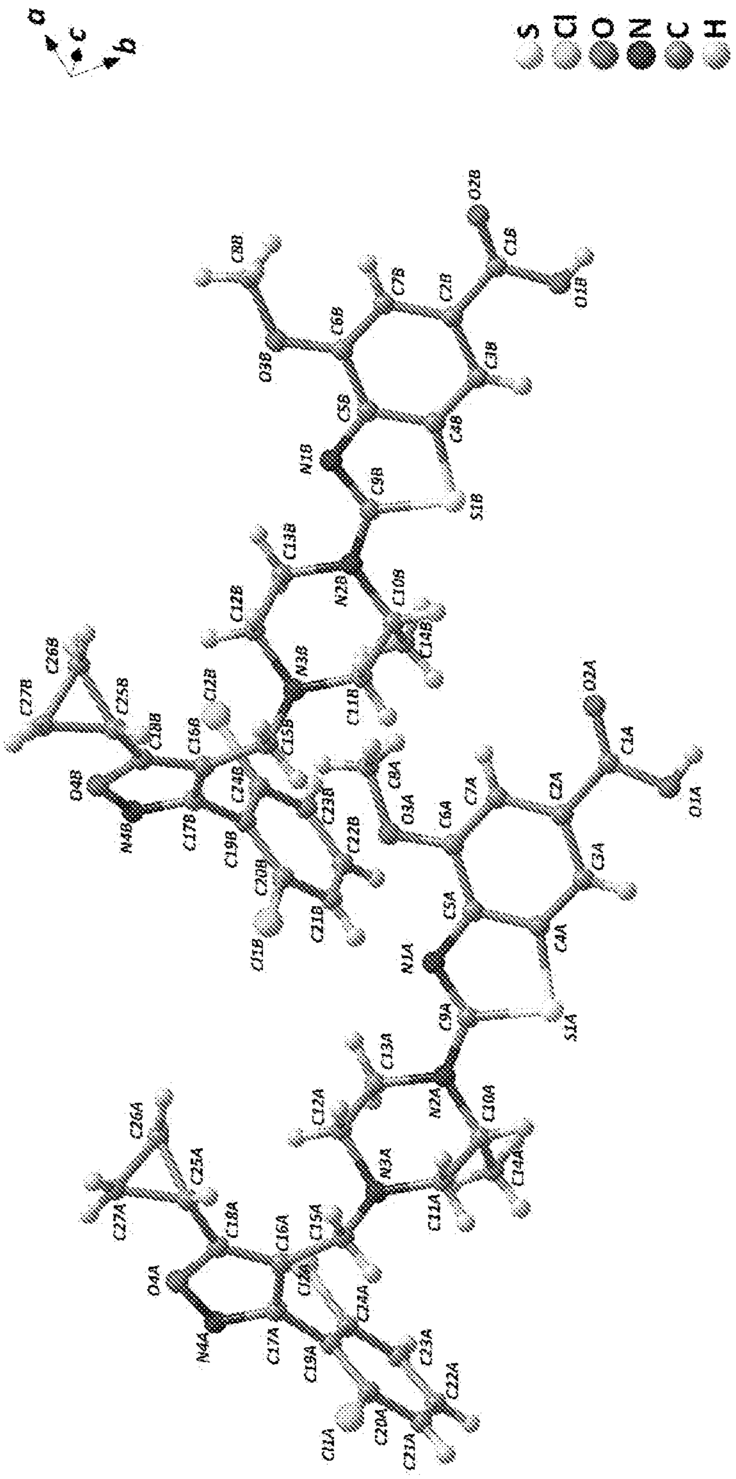
FIGS. 28A and 28B provide the asymmetric unit (FIG. 28A) and the ORTEP drawing of the first molecule in the asymmetric unit (FIG. 28B) of a single crystal analysis of the crystalline free base of Compound I (form A), according to the examples.
Figure 28B:
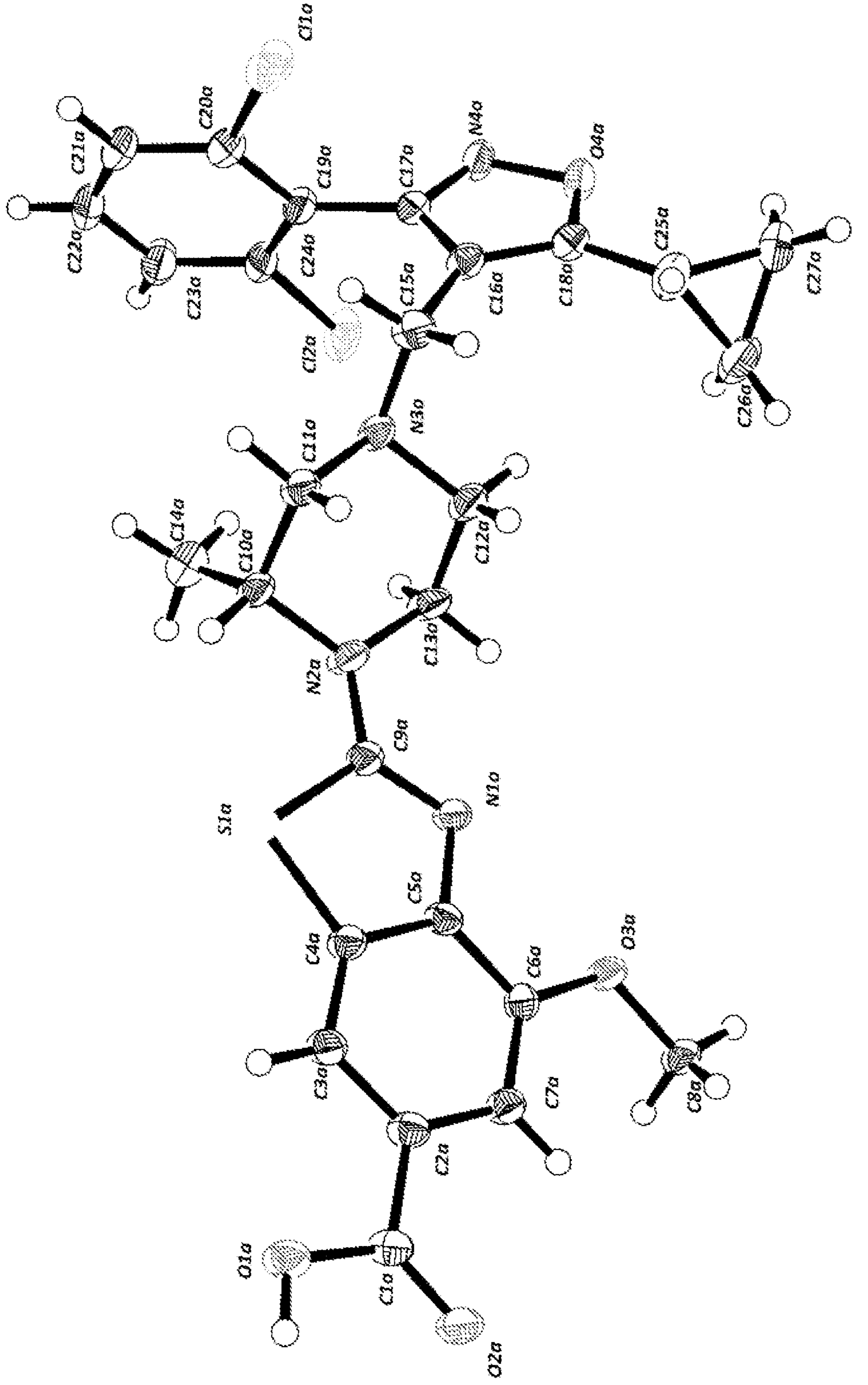

As shown in the refined structure (FIGS. 28A and 28B), the asymmetric unit of the single crystal structure includes two Compound I molecules, which indicates that form A is an anhydrate. The single crystal structure demonstrates the stereochemistry structure of compound I and the absolute configuration assignment (R/S) of the chiral atom (C10) is R. The crystal system of the single crystal is monoclinic and the space group is $P2_1$. The unit cell parameters are: {a=16.81300(10) Å, b=8.58780(10) Å, c=19.04770(10) Å, α=90°, β=94.0640(10)°, γ=90°, V=2743.32(4) $Å_3$}. Pertinent crystallographic data and the refinement parameters are summarized in Table 7B.

TABLE 7B

| Crystallographic data and refinement parameters of form A single crystal | |
|---|---|
| Empirical formula | $C_{27}H_{26}Cl_2N_4O_4S$ |
| Formula weight | 573.48 |
| Temperature | 120.00(10) K |
| Wavelength | CuKα (λ = 1.54184 Å) |
| Crystal system, space group | Monoclinic, $P2_1$ |
| Unit cell dimensions | a = 16.81300(10) Å<br>b = 8.58780(10) Å<br>c = 19.04770(10) Å<br>α= 90°<br>β = 94.0640(10)°<br>γ = 90° |
| Volume | 2743.32(4) $Å_3$ |
| Z, CalMolated density | 4, 1.389 $g/cm_3$ |
| Absorption coefficient | 3.179 $mm_{-1}$ |
| F(000) | 1192.0 |
| Crystal size | 0.348 × 0.039 × 0.012 $mm_3$ |
| 2 Theta range for data collection | 5.27 to 151.992 |
| Limiting indices | −21 ≤ h ≤ 21<br>−10 ≤ k ≤ 10<br>−23 ≤ l ≤ 23 |
| Reflections collected/ Independent reflections | 69016/11413 [$R_{int}$ = 0.0661, $R_{sigma}$ = 0.0354] |
| Refinement method | Full-matrix least-squares on $F^2$ |
| Completeness | 100% |
| Data/restraints/parameters | 11413/1/697 |
| Goodness-of-fit on $F^2$ | 1.087 |
| Final R indices [I ≥ 2sigma(I)] | $R_1$ = 0.0346, $wR_2$ = 0.0944 |
| Final R indices [all data] | $R_1$ = 0.0357, $wR_2$ = 0.0959 |
| Largest diff. peak and hole | 0.19/−0.27 e · $Å^{-3}$ |
| Flack parameter | −0.008(7) |
| Bayesian statistics on Bijvoet differences | Hooft y = −0.009(6), P2(true) = 1.000, P3(true) = 1.000, P3(rac-twin) = 0.0E+00, P3(false) = 0.0E+00, corr. coeff = 0.995 |

Using the single crystal X-ray analysis, the calculated XRPD pattern was generated for Cu radiation using a $Mercury_4$ program. The calculated pattern was consistent with the XRPD pattern of form A (FIG. 1).

Approximately 2 mg of Form A of Compound I was added into a 3-mL glass vial. At room temperature, the solvents in Table 8 were then added stepwise into the vials until the solids were dissolved visually or a total volume of 2 mL was reached. The solubility results are provided in Table 8.

TABLE 8

Approximate solubility of Form A of Compound I

| Solvent | Solubility (mg/mL) | Solvent | Solubility (mg/mL) |
|---|---|---|---|
| MeOH | 10.5 < S < 21.0 | CPME | 11.5 < S < 23.0 |
| Acetone | S > 42.0 | 2-MeTHF | S > 40.0 |
| EtOAc | 10.0 < S < 20.0 | MeOH/$H_2O$ (9:1) | 5.3 < S < 10.5 |
| THF | S > 40.0 | MIBK/n-heptane (2:1) | 4.2 < S < 7.0 |
| ACN | 4.8 < S < 9.5 | THF/n-heptane (2:1) | S > 38.0 |
| MIBK | 10.0 < S < 20.0 | CPME/n-heptane (2:1) | 2.3 < S < 4.6 |
| IPAc | 3.8 < S < 6.3 | — | — |

Example 2: Preparation and Characterization of Amorphous Form of Compound I

Method 1. A solution of compound (I) in dichloromethane (60 mg/mL) was placed at room temperature and evaporated to dryness.

Method 2. n-Hexane (50 μl) was added in a solution of compound (I) in dichloromethane (50 μl) (300 mg/mL). A clear solution was obtained and magnetically stirred for 5 days to obtain the solid.

Method 3. A solution of compound (I) in MeOH (50 μl) (300 mg/mL) was added in $H_2O$ (2 mL). A clear solution was obtained and magnetically stirred for 4 days to obtain the solid.

Figure 24:
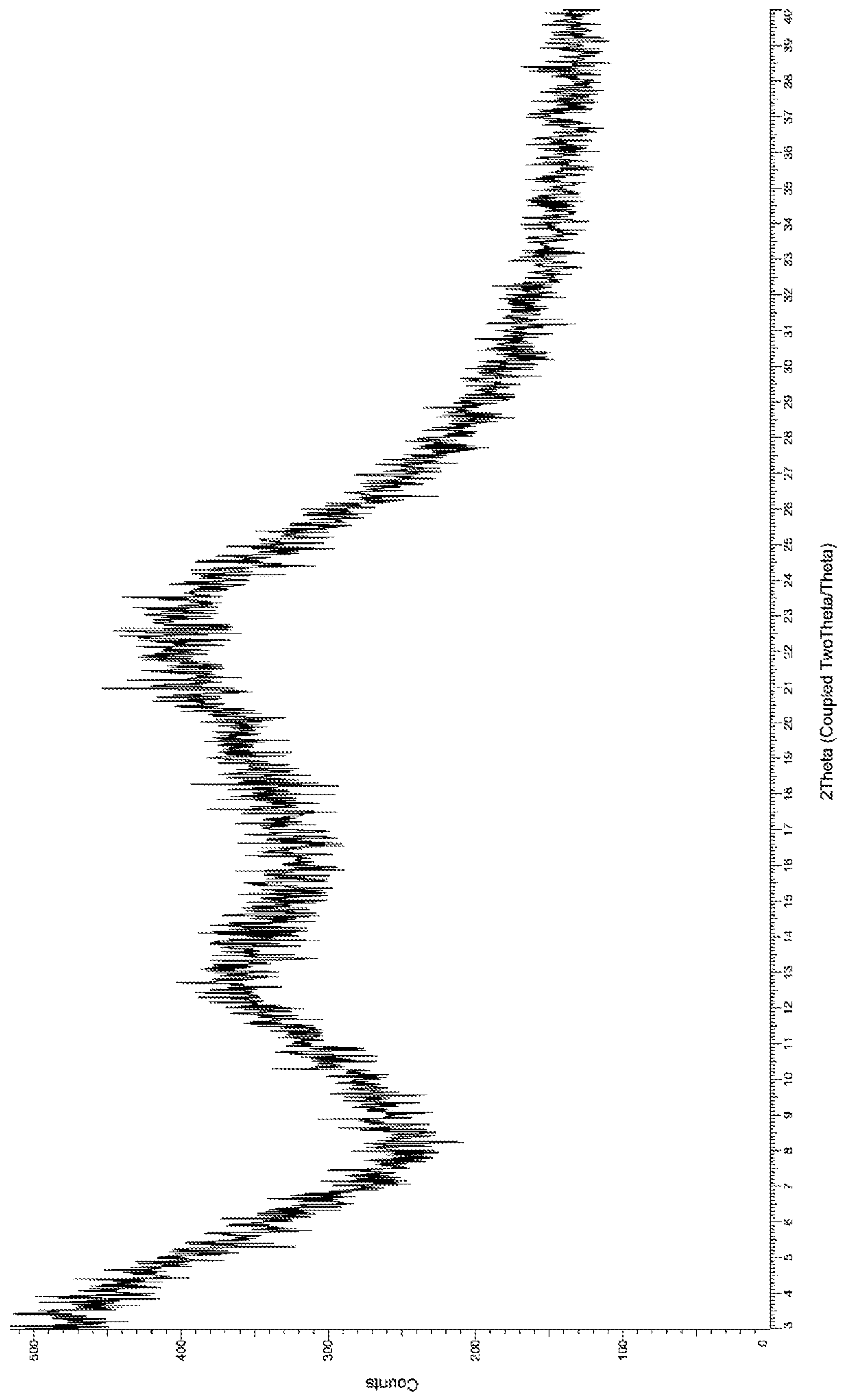
FIG. 24 provides an X-ray powder diffraction (XRPD) spectrum of amorphous Compound I, according to the examples.
Figure 25:
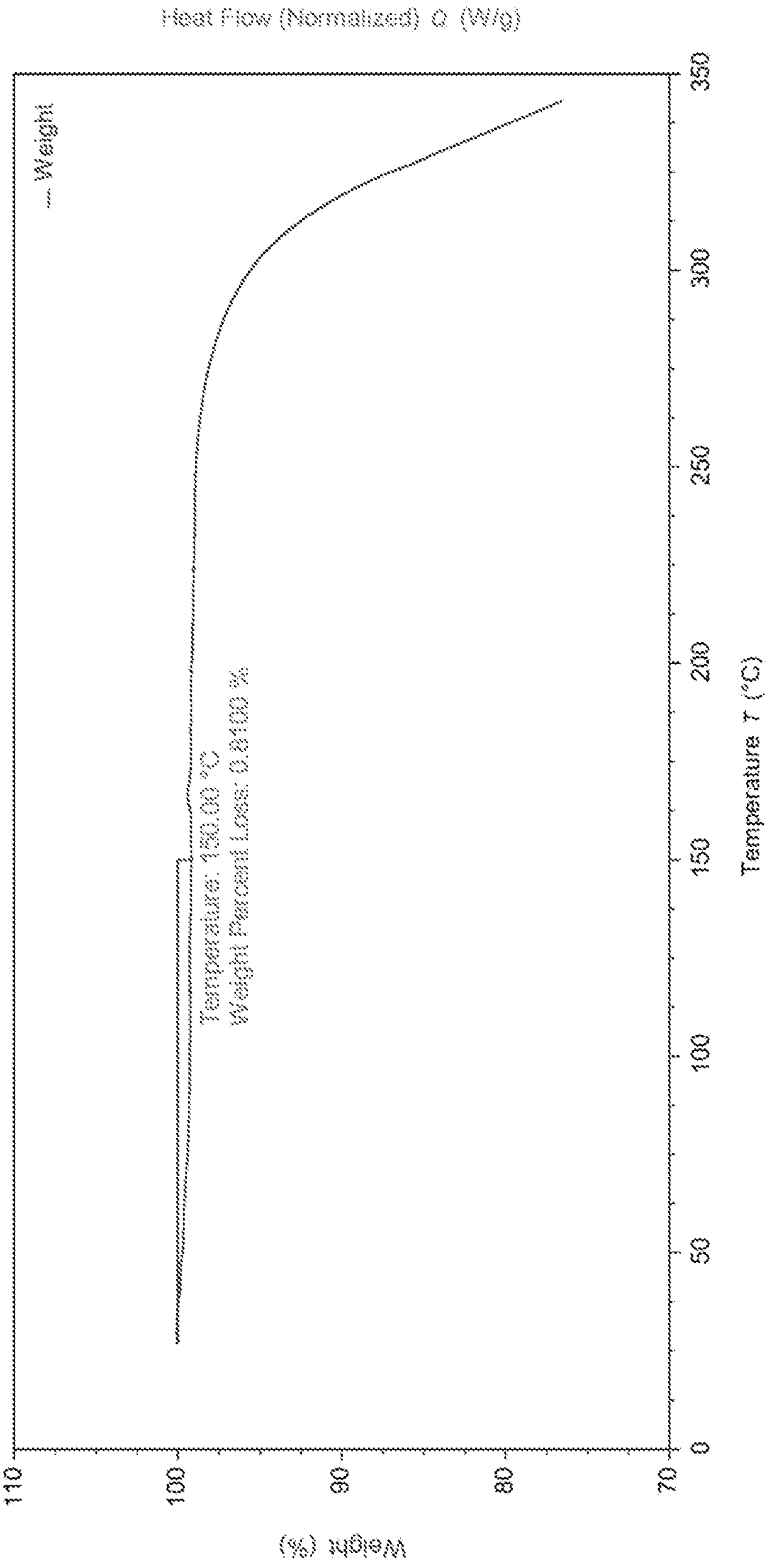
FIG. 25 provides a thermogravimetric analysis (TGA) thermogram of amorphous Compound I, according to the examples.
Figure 26:
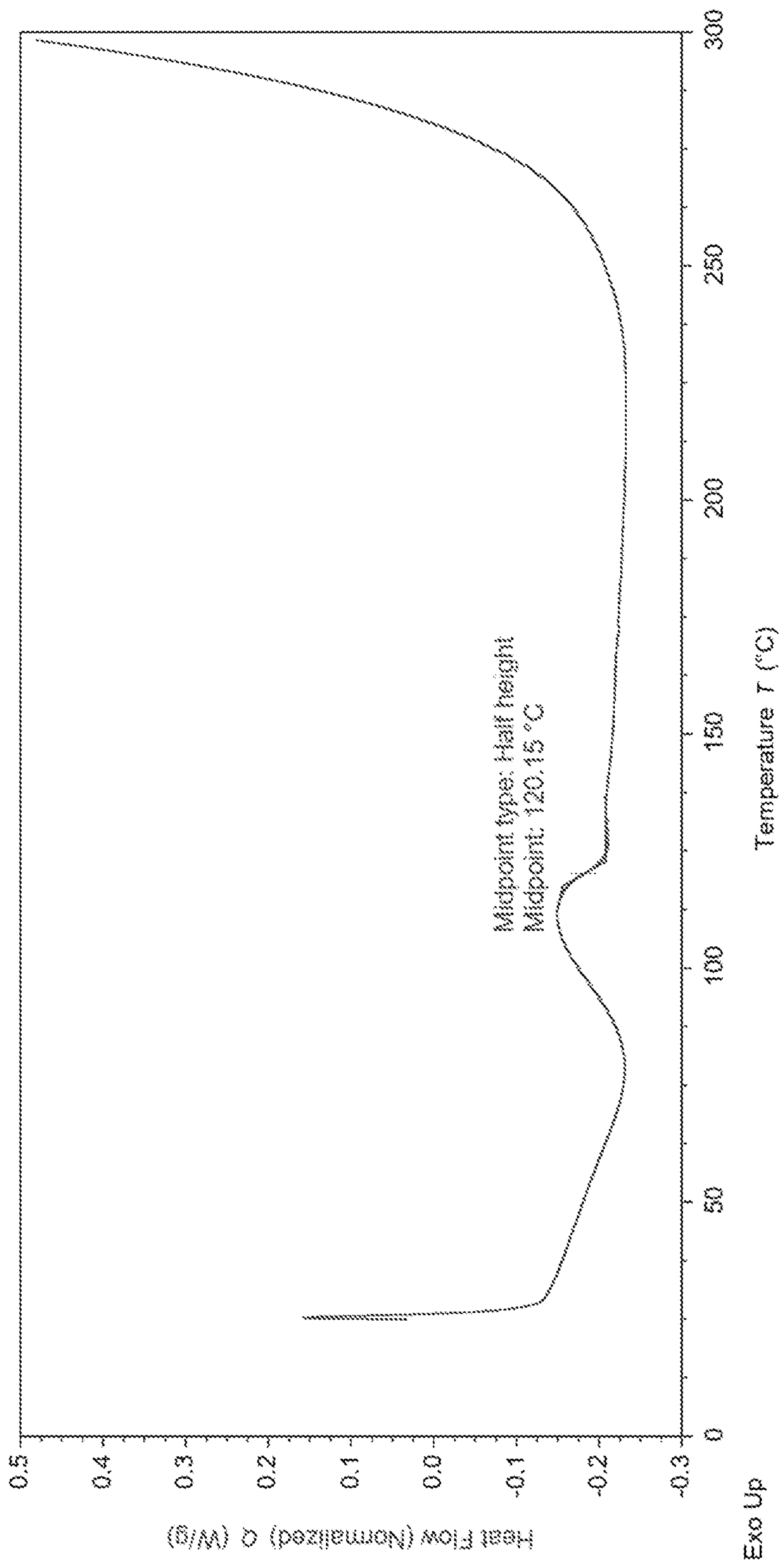
FIG. 26 provides a differential scanning calorimetry (DSC) thermogram of amorphous Compound I, according to the examples.
Figure 27:
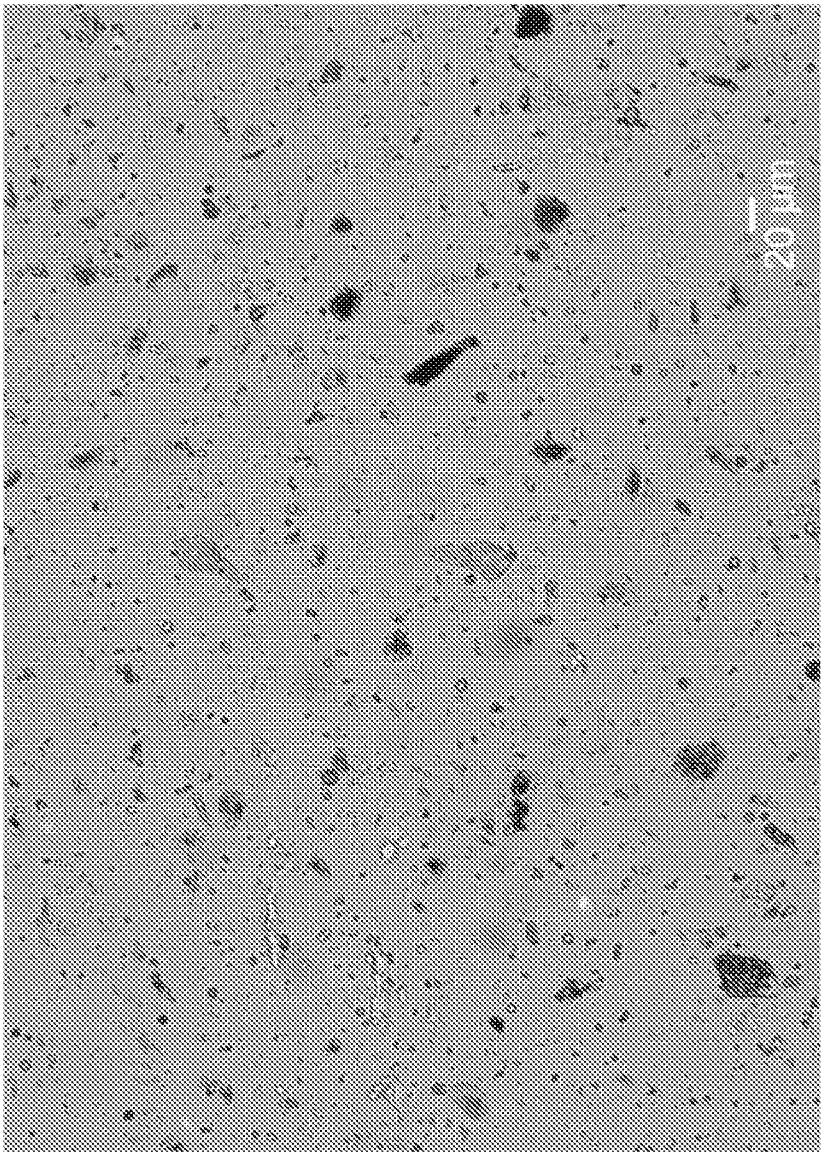
FIG. 27 provides a polarized light microscopy (PLM) image of amorphous Compound I, according to the examples.

The solid samples from each method were analyzed. The results showed that all of the obtained solid samples were amorphous. An XRPD is shown in FIG. 24 with no characteristic peaks. The TGA thermogram is provided in FIG. 25, the DSC thermogram is provided in FIG. 26, and the PLM image is provided in FIG. 27. The glass transition observed by DSC was at about 120° C. and the sample started to decompose at about 300° C. according to TGA.

Example 3: Preparation and Characterization of HCl Salt of Compound I (Form B)

Form A (576.1 mg) was added into a 20-mL glass vial followed by the addition of 14 mL of EtOAc and magnetic stirring at room temperature. To the mixture, 0.5 mL of HCl-EtOAc (2 mol/L) was added dropwise. After 4 days, the solid was isolated by vacuum filtration followed by drying at room temperature under vacuum for about 6 h. An amorphous sample was obtained. To the amorphous solid, 4 mL of ACN/$H_2O$ (19:1, v/v) was added to provide a slurry held at room temperature for 1 day. The solids were isolated by centrifugation (10000 rpm, 4 min) and dried at room temperature under vacuum for about 23 h.

The characteristic XRPD pattern is shown in FIG. 6. Peaks from the XRPD pattern are provided in Table 9.

TABLE 9

| Peak list of HCl salt (Form B) | | | |
|---|---|---|---|
| No. | Pos. [°2θ] | d-spacing [Å] | Rel. Int. [%] |
| 1 | 7.04 | 12.56 | 100.00 |
| 2 | 8.81 | 10.04 | 29.87 |
| 3 | 10.38 | 8.52 | 33.28 |
| 4 | 10.97 | 8.06 | 47.86 |
| 5 | 11.59 | 7.64 | 37.65 |
| 6 | 11.83 | 7.48 | 82.58 |
| 7 | 12.22 | 7.24 | 23.37 |
| 8 | 14.08 | 6.29 | 52.12 |
| 9 | 17.02 | 5.21 | 10.75 |
| 10 | 17.65 | 5.02 | 13.64 |
| 11 | 18.48 | 4.80 | 24.90 |
| 12 | 20.13 | 4.41 | 36.95 |
| 13 | 20.83 | 4.27 | 27.83 |
| 14 | 22.01 | 4.04 | 8.99 |
| 15 | 24.14 | 3.69 | 47.02 |
| 16 | 24.62 | 3.62 | 27.02 |
| 17 | 25.00 | 3.56 | 12.72 |
| 18 | 26.85 | 3.32 | 22.97 |
| 19 | 29.00 | 3.08 | 17.28 |
| 20 | 30.75 | 2.91 | 6.58 |

TGA analysis of Form B of Compound I provided a weight loss of 3.1% up to 130° C. The TGA thermogram is provided in FIG. 7.

DSC analysis of Form B of Compound I provided two endotherms at 101.1° C. (peak) and 184.0° C. (onset temperature). The DSC thermogram is provided in FIG. 8.

Figure 9:
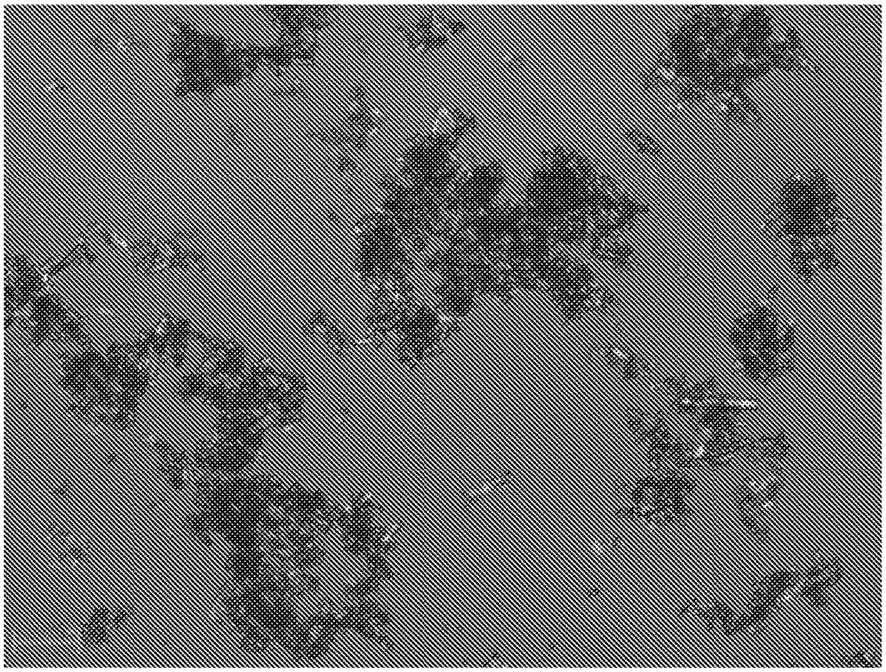
FIG. 9 provides a PLM image of the crystalline hydrochloride salt of Compound I (form B), according to the examples.

The PLM of Form B of Compound I provided rod-like particles with aggregation. The PLM image is provided in FIG. 9.

HPLC purity was determined to be 99.9 area %. IC result confirmed the molar ratio of ion/free base was 1:1.

Example 4: Preparation and Characterization of HCl Salt of Compound I (Form C)

HCl salt Form C was observed after $N_2$ purging HCl salt Form B for 20 min at 30° C. via variable-temperature XRPD (VT-XRPD) shown in FIG. 22. Peaks from the XRPD pattern are provided in Table 10.

After further heating to 120° C. and cooling to 30° C. with $N_2$ protection, no form change occurred. HCl salt Form B was re-obtained after exposing Form C to ambient conditions for about 10 min. Based on data above, it would convert to dehydrate state (HCl salt Form C) at low humidity and back to hydrate at high humidity.

TABLE 10

| Peak list of HCl salt (Form C) | | | |
|---|---|---|---|
| No. | Pos. [°2θ] | d-spacing [Å] | Rel. Int. [%] |
| 1 | 7.16 | 12.35 | 33.52 |
| 2 | 8.95 | 9.88 | 14.13 |
| 3 | 9.57 | 9.24 | 14.93 |
| 4 | 10.57 | 8.37 | 40.56 |
| 5 | 11.20 | 7.90 | 7.97 |
| 6 | 12.08 | 7.32 | 77.12 |
| 7 | 12.30 | 7.20 | 48.06 |
| 8 | 13.13 | 6.74 | 9.22 |
| 9 | 14.25 | 6.22 | 49.95 |
| 10 | 14.58 | 6.08 | 22.08 |
| 11 | 16.54 | 5.36 | 29.56 |
| 12 | 16.86 | 5.26 | 17.92 |
| 13 | 17.29 | 5.13 | 33.03 |
| 14 | 18.01 | 4.92 | 29.41 |
| 15 | 18.87 | 4.70 | 51.11 |

TABLE 10-continued

| Peak list of HCl salt (Form C) | | | |
|---|---|---|---|
| No. | Pos. [°2θ] | d-spacing [Å] | Rel. Int. [%] |
| 16 | 20.17 | 4.40 | 41.56 |
| 17 | 20.44 | 4.35 | 51.60 |
| 18 | 21.28 | 4.17 | 58.84 |
| 19 | 21.40 | 4.15 | 54.86 |
| 20 | 21.66 | 4.10 | 30.01 |
| 21 | 22.02 | 4.04 | 30.46 |
| 22 | 23.04 | 3.86 | 26.84 |
| 23 | 23.48 | 3.79 | 33.81 |
| 24 | 24.57 | 3.62 | 100.00 |
| 25 | 25.25 | 3.53 | 60.74 |
| 26 | 26.46 | 3.37 | 23.58 |
| 27 | 26.81 | 3.33 | 25.43 |
| 28 | 27.40 | 3.25 | 48.35 |
| 29 | 27.77 | 3.21 | 19.95 |
| 30 | 29.53 | 3.03 | 24.00 |
| 31 | 30.18 | 2.96 | 15.90 |
| 32 | 31.98 | 2.80 | 11.06 |
| 33 | 32.35 | 2.77 | 11.39 |
| 34 | 33.34 | 2.69 | 8.37 |
| 35 | 34.09 | 2.63 | 3.85 |

Example 5: Preparation and Characterization of HBr Salt of Compound I (Form D)

Form A (500.3 mg) was added into a 20-mL glass vial followed by the addition of 12 mL of MIBK/n-heptane (2:1, v/v) and magnetic stirring at room temperature. To the mixture, 125 μL of aqueous HBr (40 wt %) was added dropwise. After 2 days, the solid was isolated by vacuum filtration followed by drying at 50° C. under vacuum for about 10.5 h.

The characteristic XRPD pattern is shown in FIG. 11. Peaks from the XRPD pattern are provided in Table 11.

TABLE 11

| Peak list of HBr salt (Form D) | | | |
|---|---|---|---|
| No. | Pos. [°2θ] | d-spacing [Å] | Rel. Int. [%] |
| 1 | 8.99 | 9.84 | 68.09 |
| 2 | 10.54 | 8.39 | 25.41 |
| 3 | 11.85 | 7.47 | 59.99 |
| 4 | 12.29 | 7.20 | 24.29 |
| 5 | 14.18 | 6.25 | 35.08 |
| 6 | 14.55 | 6.09 | 21.79 |
| 7 | 16.62 | 5.33 | 26.10 |
| 8 | 17.25 | 5.14 | 26.30 |
| 9 | 17.97 | 4.94 | 32.34 |
| 10 | 18.81 | 4.72 | 28.69 |
| 11 | 20.20 | 4.40 | 41.08 |
| 12 | 20.44 | 4.35 | 37.90 |
| 13 | 21.33 | 4.17 | 25.71 |
| 14 | 23.38 | 3.81 | 31.36 |
| 15 | 24.53 | 3.63 | 100.00 |
| 16 | 25.04 | 3.56 | 37.03 |
| 17 | 27.21 | 3.28 | 32.37 |
| 18 | 28.92 | 3.09 | 17.61 |
| 19 | 29.65 | 3.01 | 18.73 |
| 20 | 35.27 | 2.54 | 5.46 |

TGA analysis of Form D of Compound I provided a weight loss of 5.3% up to 180° C. The TGA thermogram is provided in FIG. 12.

DSC analysis of Form D of Compound I provided two endotherms at 110.3° C. (peak) and 210.9° C. (onset temperature). The DSC thermogram is provided in FIG. 13.

Figure 14:
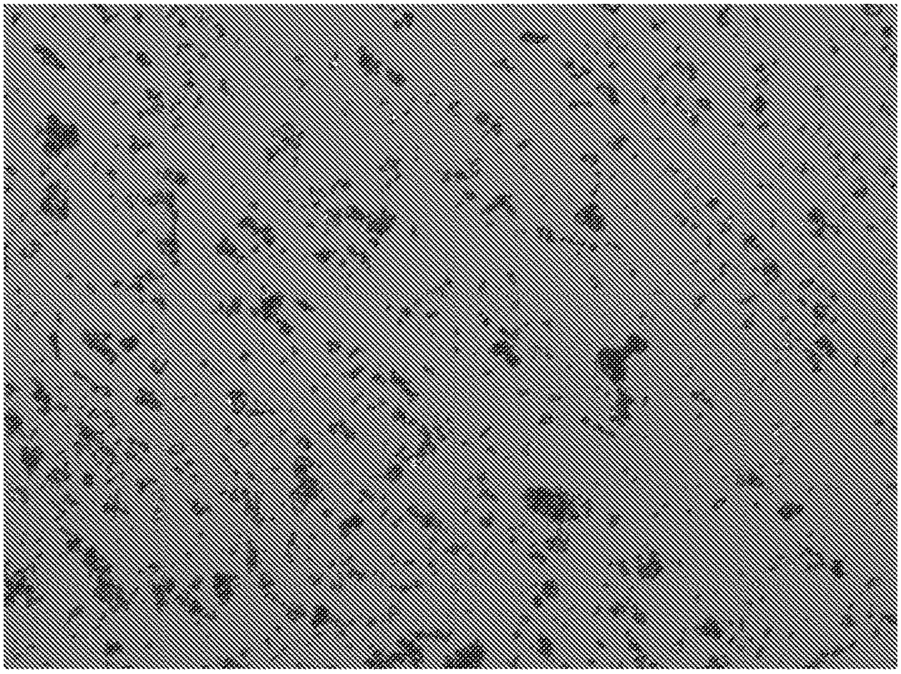
FIG. 14 provides a PLM image of the crystalline hydrobromide salt of Compound I (form D), according to the examples.

The PLM of Form D of Compound I provided irregular particles with aggregation. The PLM image is provided in FIG. 14.

HPLC purity was determined to be 99.8 area %. IC result confirmed the molar ratio of ion/free base was 1.1:1.0.

Example 6: Preparation and Characterization of HBr Salt of Compound I (Form E)

HBr salt Form E was observed after $N_2$ purging HBr salt Form D for 20 min at 30° C. via variable-temperature XRPD (VT-XRPD) shown in FIG. 23. Peaks from the XRPD pattern are provided in Table 12.

After further heating to 120° C. and cooling to 30° C. with $N_2$ protection, no form change occurred. HBr salt Form D was re-obtained after exposing Form E to ambient conditions for about 10 min. Based on data above, it would convert to dehydrate state (HBr salt Form E) at low humidity and back to hydrate at high humidity.

TABLE 12

Peak list of HBr salt (Form E)

| No. | Pos. [°2θ] | d-spacing [Å] | Rel. Int. [%] |
|---|---|---|---|
| 1 | 6.55 | 13.49 | 4.87 |
| 2 | 8.99 | 9.84 | 35.91 |
| 3 | 9.60 | 9.22 | 8.36 |
| 4 | 10.56 | 8.38 | 33.06 |
| 5 | 11.95 | 7.41 | 51.57 |
| 6 | 12.31 | 7.19 | 19.43 |
| 7 | 14.08 | 6.29 | 20.85 |
| 8 | 14.28 | 6.20 | 33.23 |
| 9 | 14.60 | 6.07 | 29.57 |
| 10 | 15.21 | 5.83 | 12.65 |
| 11 | 16.60 | 5.34 | 33.11 |
| 12 | 16.75 | 5.29 | 27.71 |
| 13 | 17.27 | 5.13 | 33.24 |
| 14 | 17.74 | 5.00 | 21.02 |
| 15 | 18.04 | 4.92 | 49.80 |
| 16 | 18.89 | 4.70 | 40.27 |
| 17 | 20.17 | 4.40 | 36.93 |
| 18 | 20.47 | 4.34 | 44.10 |
| 19 | 21.44 | 4.14 | 32.34 |
| 20 | 21.87 | 4.06 | 24.42 |
| 21 | 22.31 | 3.99 | 16.98 |
| 22 | 22.99 | 3.87 | 28.91 |
| 23 | 23.29 | 3.82 | 46.48 |
| 24 | 23.93 | 3.72 | 21.32 |
| 25 | 24.60 | 3.62 | 100.00 |
| 26 | 24.96 | 3.57 | 46.91 |
| 27 | 25.24 | 3.53 | 45.92 |
| 28 | 25.41 | 3.51 | 52.36 |
| 29 | 26.10 | 3.41 | 23.38 |
| 30 | 26.51 | 3.36 | 25.20 |
| 31 | 27.38 | 3.26 | 49.79 |
| 32 | 27.78 | 3.21 | 31.56 |
| 33 | 29.21 | 3.06 | 31.83 |
| 34 | 29.46 | 3.03 | 29.40 |
| 35 | 29.87 | 2.99 | 34.43 |
| 36 | 30.67 | 2.91 | 21.50 |
| 37 | 30.98 | 2.89 | 25.45 |
| 38 | 31.64 | 2.83 | 20.25 |
| 39 | 32.34 | 2.77 | 26.25 |
| 40 | 32.88 | 2.72 | 19.60 |
| 41 | 33.64 | 2.66 | 23.89 |
| 42 | 34.94 | 2.57 | 19.30 |
| 43 | 35.82 | 2.51 | 20.56 |
| 44 | 36.99 | 2.43 | 20.76 |
| 45 | 38.43 | 2.34 | 18.56 |
| 46 | 39.46 | 2.28 | 18.30 |

Example 7: Preparation and Characterization of Edisylate Salt of Compound I (Form F)

Form A (1 eq.) was added into a 20-mL glass vial followed by the addition of 1,2-ethanedisulfonic acid (5 eq), and MIBK/n-heptane (2:1, v/v) and magnetic stirring at room temperature. After 3 days, the solid was isolated by vacuum filtration followed by drying at room temperature under vacuum for about 1 day.

The characteristic XRPD pattern is shown in FIG. 16. Peaks from the XRPD pattern are provided in Table 13.

TABLE 13

Peak list of Edisylate salt (Form F)

| No. | Pos. [°2θ] | d-spacing [Å] | Rel. Int. [%] |
|---|---|---|---|
| 1 | 6.69 | 13.21 | 70.57 |
| 2 | 13.41 | 6.60 | 100.00 |
| 3 | 14.42 | 6.14 | 92.86 |
| 4 | 23.36 | 3.81 | 35.32 |
| 5 | 24.72 | 3.60 | 25.03 |
| 6 | 27.06 | 3.29 | 21.10 |

TGA analysis of Form F of Compound I provided a weight loss of 9.1% up to 200° C. The TGA thermogram is provided in FIG. 17.

DSC analysis of Form F of Compound I provided two endotherms at 120.9° C. (peak) and 204.1° C. (onset temperature). The DSC thermogram is provided in FIG. 18.

$^1$H NMR spectrum showed the molar ratio of acid/free base was 0.7:1 and solvent MIBK/API is 0.5:1 (6.2 wt %). Based on the stepwise TGA weight loss, corresponding DSC endotherm, and solvent content by $^1$H NMR, the Edisylate Form F is speculated to be an MIBK solvate.

Example 8: Preparation and Characterization of Mesylate Salt of Compound I (Form G)

Form A (19.9 mg) was added into a 20-mL glass vial followed by the addition of methanesulfonic acid (3.4 mg) and EtOAc (0.5 mL) and magnetic stirring at room temperature. After 3 days, the solid was isolated by vacuum filtration followed by drying at room temperature under vacuum for about 1 day.

The characteristic XRPD pattern is shown in FIG. 19. Peaks from the XRPD pattern are provided in Table 14.

TABLE 14

Peak list of Mesylate salt (Form G)

| No. | Pos. [°2θ] | d-spacing [Å] | Rel. Int. [%] |
|---|---|---|---|
| 1 | 9.54 | 9.27 | 100.00 |
| 2 | 16.84 | 5.26 | 4.13 |
| 3 | 19.23 | 4.61 | 3.87 |
| 4 | 22.33 | 3.98 | 12.53 |
| 5 | 22.96 | 3.87 | 17.96 |
| 6 | 25.80 | 3.45 | 8.43 |

TGA analysis of Form G of Compound I provided a weight loss of 7.6% up to 160° C. The TGA thermogram is provided in FIG. 20.

DSC analysis of Form G of Compound I provided two endotherms at 92.2° C. (peak) and 138.3° C. (onset temperature). The DSC thermogram is provided in FIG. 21.

$^1$H NMR spectrum showed the molar ratio of acid/free base was 0.9:1 and solvent EtOAc/API is 0.5:1 (6.2 wt %). A weakly crystalline sample was obtained after heating Mesylate Form G to 120° C. and cooling to room temperature to remove solvent. Based on all the results, Mesylate Form G is speculated to be an EtOAc solvate.

Example 9: Kinetic Solubility of Free Base (form A), HCl Salt (form B), and HBr Salt (Form D) in Water and Three Bio-Relevant Media (SGF, FaSSIF and FeSSIF) at 37° C.

About 20 mg of free base (form A) HCl salt (form B), and HBr salt (form D) were added to a 5-mL glass vials followed by the addition of 4 mL of the corresponding medium/solvent into each glass vial to form a suspension. The vials were capped and rolled at 37° C. (25 rpm). Samples were removed (1 mL) at 1 h, 4 h, and 24 h and centrifuged (14000 rpm, 2 min, room temperature). The supernatant was filtered through 0.22 μm syringe filter (first few drops of filtrate were discarded) for HPLC solubility and pH tests (Table 15). The residual solids were analyzed by XRPD.

TABLE 15

Kinetic solubility results

| | | 1 hr | | | 4 hrs | | | 24 hrs | | |
|---|---|---|---|---|---|---|---|---|---|---|
| Material | Medium | FC | S | pH | FC | S | pH | FC | S | pH |
| HCl salt | $H_2O$ | No | 0.0049 | 6.1 | No | 0.0056 | 5.9 | No | 0.0061 | 6.4 |
| Form B | SGF | No | 0.061 | 1.8 | No | 0.048 | 1.9 | Yes | 0.039 | 1.8 |
| | FaSSIF | No | 0.29 | 6.5 | No | 0.42 | 6.5 | No | 0.57 | 6.4 |
| | FeSSIF | No | 0.48 | 5.1 | No | 0.48 | 5.0 | No | 0.50 | 5.0 |
| HBr salt | $H_2O$ | No | 0.0006 | 3.0 | No | 0.0007 | 3.0 | No | 0.0006 | 3.0 |
| Form D | SGF | No | 0.031 | 1.9 | No | 0.030 | 1.9 | Yes | 0.043 | 1.7 |
| | FaSSIF | No | 0.32 | 6.3 | No | 0.46 | 6.3 | No | 0.64 | 6.3 |
| | FeSSIF | No | 0.66 | 5.1 | No | 0.71 | 5.1 | No | 0.78 | 5.0 |
| Form A | $H_2O$ | No | 0.003 | 6.2 | No | 0.0023 | 6.3 | No | 0.0046 | 6.4 |
| | SGF | No | 0.020 | 2.1 | No | 0.018 | 1.8 | No | 0.017 | 2.0 |
| | FaSSIF | No | 0.016 | 6.4 | No | 0.017 | 6.5 | No | 0.022 | 6.4 |
| | FeSSIF | No | 0.051 | 5.0 | No | 0.056 | 5.1 | No | 0.056 | 5.1 |

S: solubility (mg/mL). FC: form change (Yes: form changed. No: form not changed).

As provided in Table 15, the solubility of free base (form A), HCl salt (form B), and HBr salt (form D) in water was relative low (<7 μg/mL) with HBr salt (form D) showing the lowest solubility. Compared with free base (form A) and HCl salt (form B), HBr salt (form D) showed improved solubility in SGF, FaSSIF, and FeSSIF. In particular, significant solubility improvement was observed in FaSSIF and FeSSIF for HCl salt (form B) and HBr salt (form D).

Example 10: Solid State Stability of Free Base (form A), HCl Salt (form B), and HBr Salt (Form D)

All the samples were characterized by XRPD for physical stability and HPLC purity for chemical stability evaluation (Table 16).

TABLE 16

Solid state stability results

| | Initial | 80° C./1 day | | 25° C./60% RH/ 1 week | | 40° C./75% RH/ 1 week | |
|---|---|---|---|---|---|---|---|
| Sample | purity (area %) | Purity/initial purity (%) | Form change | Purity/initial purity (%) | Form change | Purity/initial purity (%) | Form change |
| HCl salt Form B | 99.9 | 100.0 | No | 100.0 | No | 100.0 | No |
| HBr salt Form D | 99.8 | 99.5 | No | 99.9 | No | 99.9 | No |
| Form A | 99.9 | 99.8 | No | 100.0 | No | 99.9 | No |

As provided in Table 16, free base (form A) and the HCl salt (form B) did not experience any form changes or decrease in purity under all the conditions, which indicates free base (form A) and the HCl salt (form B) exhibited good solid state stability under the test conditions. For HBr salt (form D), no form change was observed, but HPLC purity decreased after stored under 80° C. for 1 day.

Example 11: Hygroscopicity of Free Base (Form A), HCl Salt (Form B), and HBr Salt (Form D)

Figure 5:
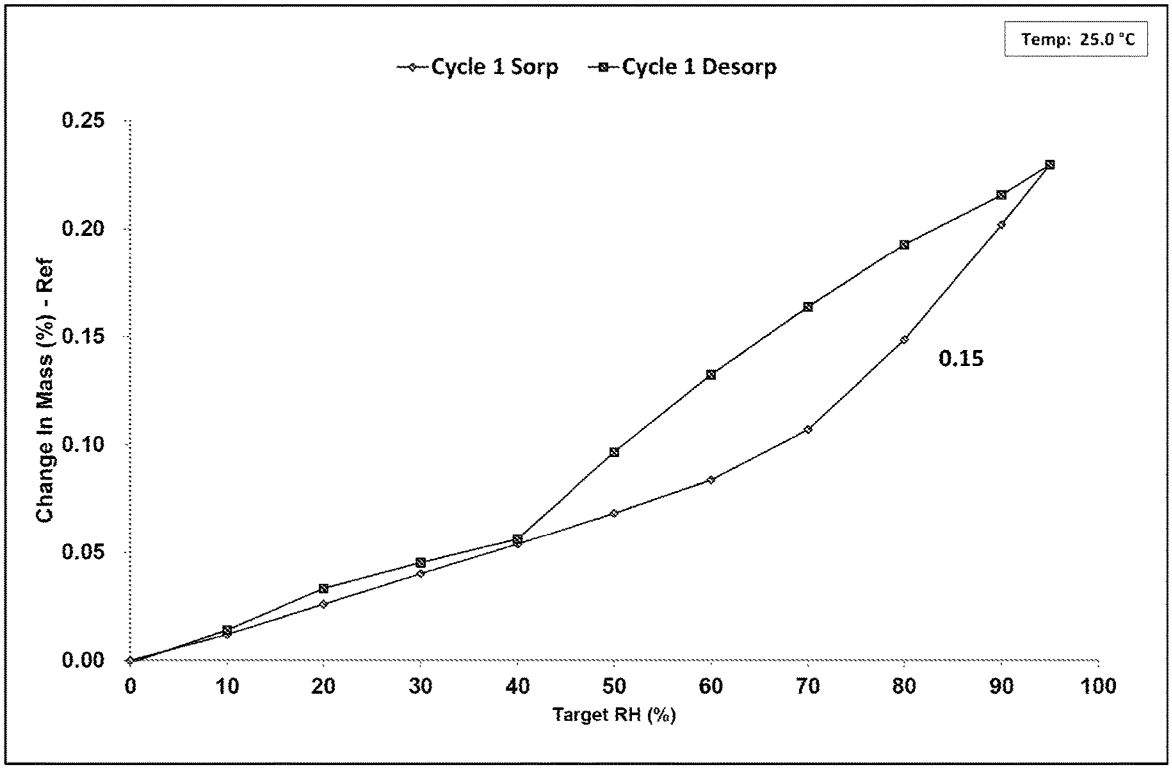
FIG. 5 provides a dynamic vapor sorption (DVS) plot of the crystalline free base of Compound I (form A), according to the examples.

For free base (form A), the water sorption isotherms between 0 and 95% RH recorded at 25° C. are provided in FIG. 5. The water uptake at 80% RH is 0.15%, which indicates that Form A is non-hygroscopic.

Figure 10:
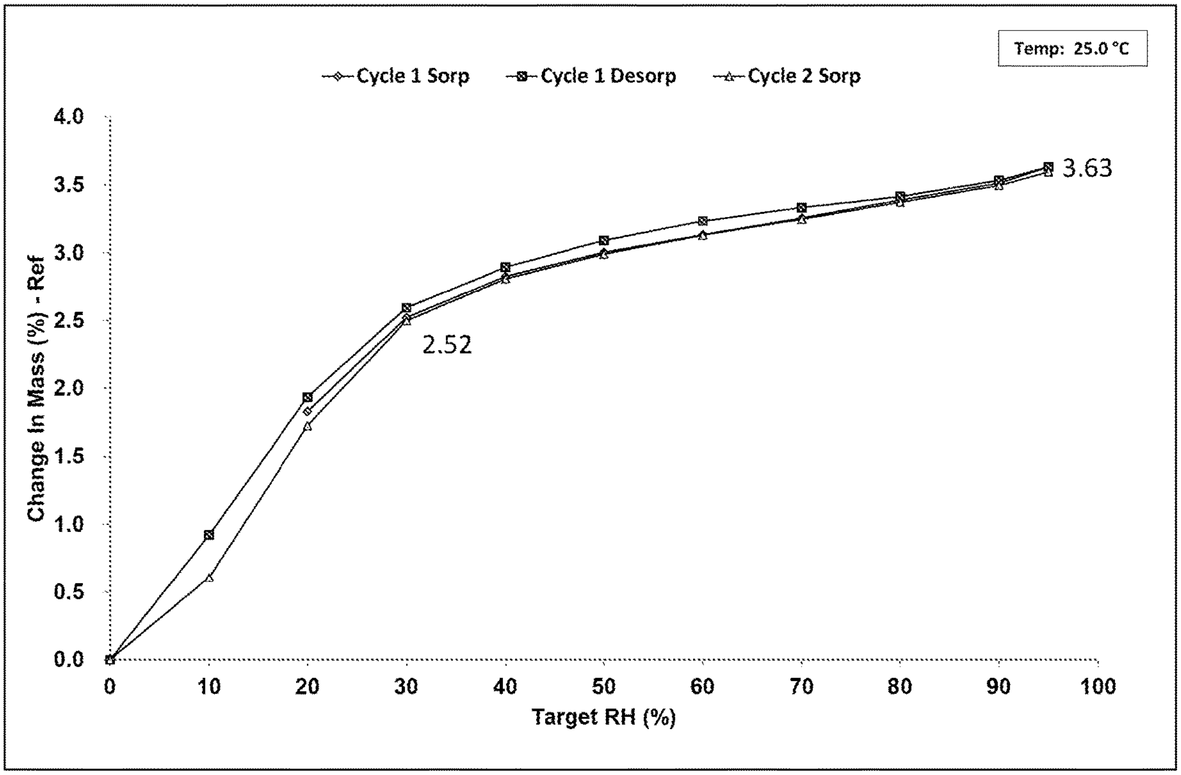
FIG. 10 provides a DVS plot of the crystalline hydrochloride salt of Compound I (form B), according to the examples.

For the HCl salt (form B), the water sorption isotherms between 0 and 95% RH recorded at 25° C. are provided in FIG. 10. The water uptake increased to 2.5% in the range of 0% RH to 30% RH and a platform could be observed between 30% RH and 95% RH. The DVS result suggested that HCl salt (form B) as a hydrate might convert to anhydrous state at low humidity, which converted back to HCl salt (form B) at higher humidity.

Figure 15:
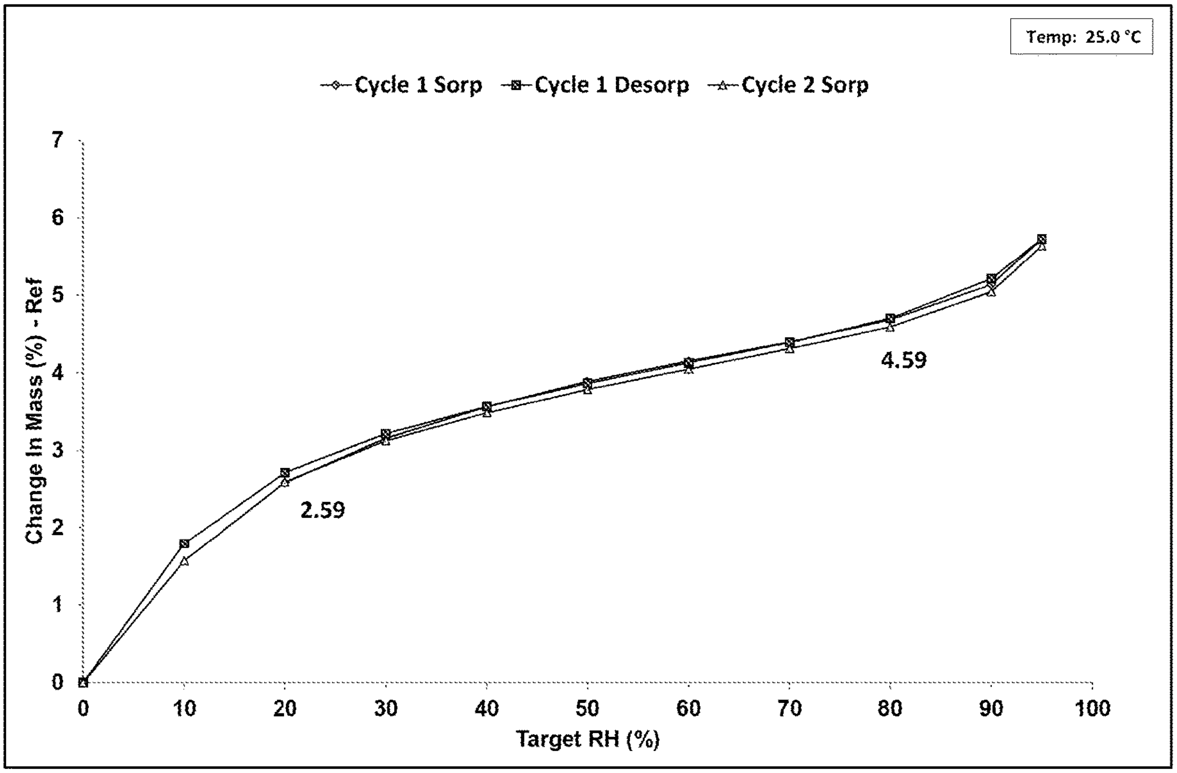
FIG. 15 provides a DVS plot of the crystalline hydrobromide salt of Compound I (form D), according to the examples.

For the HBr salt (form D), the water sorption isotherms between 0 and 95% RH recorded at 25° C. are provided in FIG. 15. The water uptake increased to 2.6% in the range of 0% RH to 20% RH and a platform could be observed between 20% RH and 80% RH. The DVS result suggested that HBr salt (form D) as a hydrate might convert to anhydrous state (form E) at low humidity, which converted back to HBr salt (form D) at higher humidity.

EQUIVALENTS

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A crystalline compound selected from a crystalline free base or a crystalline hydrochloride, hydrobromide, edisylate, or mesylate salt of Compound I:

I

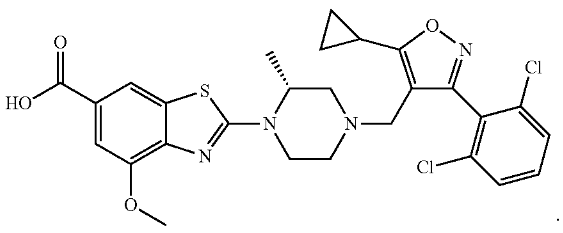

2. The crystalline compound of claim 1, wherein the compound is the crystalline free base having an X-ray powder diffraction pattern comprising one or more characteristic peaks, in terms of 2θ, at about 14.48°, about 13.48, and about 24.77.

3. The crystalline compound of claim 2, wherein the X-ray powder diffraction pattern of the crystalline free base further comprises one or more characteristic peaks, in terms of 2θ, at about 23.42°, about 6.77, and about 27.12.

4. The crystalline compound of claim 2, wherein the X-ray powder diffraction pattern of the crystalline free base further comprises one or more characteristic peaks, in terms of 2θ, at about 18.89°, about 21.24, about 21.93, and about 20.63.

5. The crystalline compound of claim 2 having an X-ray powder diffraction pattern substantially as shown in FIG. 1.

6. The crystalline compound of claim 2 having a differential scanning calorimetry thermogram showing an onset at about 212.9° C.

7. The crystalline compound of claim 6 having a differential scanning calorimetry thermogram substantially as shown in FIG. 3.

8. The crystalline compound of claim 1, wherein the compound is the crystalline hydrochloride salt having an X-ray powder diffraction pattern comprising one or more characteristic peaks, in terms of 2θ, at about 7.04°, about 11.83, and about 14.08.

9. The crystalline compound of claim 8, wherein the X-ray powder diffraction pattern of the crystalline hydrochloride salt further comprises one or more characteristic peaks, in terms of 2θ, at about 10.97°, about 24.14, and about 37.65.

10. The crystalline compound of claim 8, wherein the X-ray powder diffraction pattern of the crystalline hydrochloride salt further comprises one or more characteristic peaks, in terms of 2θ, at about 36.95°, about 10.98, about 8.81, and about 24.62.

11. The crystalline compound of claim 8 having an X-ray powder diffraction pattern substantially as shown in FIG. 6.

12. The crystalline compound of claim 8 having a differential scanning calorimetry thermogram showing an onset at about 101.1° C. and/or about 184° C.

13. The crystalline compound of claim 12 having a differential scanning calorimetry thermogram substantially as shown in FIG. 8.

14. The crystalline compound of claim 1, wherein the compound is the crystalline hydrobromide salt having an X-ray powder diffraction pattern comprising one or more characteristic peaks, in terms of 2θ, at about 24.53°, about 8.99, and about 11.85.

15. The crystalline compound of claim 14, wherein the X-ray powder diffraction pattern of the crystalline hydrobromide salt further comprises one or more characteristic peaks, in terms of 2θ, at about 20.20°, about 20.44, and about 25.04.

16. The crystalline compound of claim 14, wherein the X-ray powder diffraction pattern of the crystalline hydrobromide salt further comprises one or more characteristic peaks, in terms of 2θ, at about 14.18°, about 17.97, about 27.21, and about 23.28.

17. The crystalline form of claim 14 having an X-ray powder diffraction pattern substantially as shown in FIG. 11.

18. The crystalline compound of claim 14 having a differential scanning calorimetry thermogram showing an onset at about 110.3° C. and/or about 210.9° C.

19. The crystalline compound of claim 18 having a differential scanning calorimetry thermogram substantially as shown in FIG. 13.

20. The crystalline compound of claim 1, wherein the compound is the crystalline edisylate salt having an X-ray powder diffraction pattern comprising one or more characteristic peaks, in terms of 2θ, at about 13.41°, about 14.42, and about 6.69.

21. The crystalline compound of claim 20, wherein the X-ray powder diffraction pattern of the crystalline edisylate salt further comprises one or more characteristic peaks, in terms of 2θ, at about 23.36°, about 24.72, and about 27.06.

22. The crystalline form of claim 20 having an X-ray powder diffraction pattern substantially as shown in FIG. 16.

23. The crystalline compound of claim 20 having a differential scanning calorimetry thermogram showing an onset at about 120.9° C. and/or about 204.1° C.

24. The crystalline compound of claim 23 having a differential scanning calorimetry thermogram substantially as shown in FIG. 18.

25. The crystalline compound of claim 1, wherein the compound is the crystalline mesylate salt having an X-ray powder diffraction pattern comprising one or more characteristic peaks, in terms of 2θ, at about 9.54°, about 22.96, and about 22.33.

26. The crystalline compound of claim 25, wherein the X-ray powder diffraction pattern of the crystalline mesylate salt further comprises one or more characteristic peaks, in terms of 2θ, at about 25.80°, about 16.84, and about 19.23.

27. The crystalline form of claim 25 having an X-ray powder diffraction pattern substantially as shown in FIG. 19.

28. The crystalline compound of claim 25 having a differential scanning calorimetry thermogram showing an onset at about 92.2° C. and/or about 138.3° C.

29. The crystalline compound of claim 28 having a differential scanning calorimetry thermogram substantially as shown in FIG. 21.

30. A pharmaceutical composition comprising an effective amount of the compound of claim 1 for treating an FXR-mediated disorder or condition.

31. The pharmaceutical composition of claim 30 wherein the disorder or condition is selected from the group consisting of hepatitis B, liver disease, hyperlipidemia, hypercholesteremia, obesity, metabolic syndrome, cardiovascular disease, gastrointestinal disease, atherosclerosis, and renal disease.

32. The pharmaceutical composition of claim 31 wherein the disorder or condition is a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

33. A method of treatment comprising administering an effective amount of a compound of claim 1, or administering a pharmaceutical composition comprising an effective amount of a compound of claim 1, to a subject suffering from an FXR-mediated disorder or condition.

34. The method of claim 33, wherein the disorder or condition is selected from the group consisting of hepatitis B, liver disease, hyperlipidemia, hypercholesteremia, obesity, metabolic syndrome, cardiovascular disease, gastrointestinal disease, atherosclerosis, and renal disease.

35. The method of claim 34, wherein the disorder or condition is a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

36. A method comprising modulating FXR by contacting FXR with an effective amount of a compound of claim 1.

* * * * *